(12) United States Patent
Asmus et al.

(10) Patent No.: US 6,534,069 B1
(45) Date of Patent: *Mar. 18, 2003

(54) STABLE HYDROALCOHOLIC COMPOSITIONS

(75) Inventors: Robert A. Asmus, Hudson, WI (US); Matthew T. Scholz, Woodbury, MN (US); Jill R. Charpentier, Minnetonka, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/327,978

(22) Filed: Jun. 8, 1999

Related U.S. Application Data

(63) Continuation of application No. 08/781,565, filed on Jan. 9, 1997, now Pat. No. 6,090,395, which is a continuation-in-part of application No. 08/493,695, filed on Jun. 22, 1995, now abandoned.

(51) Int. Cl.$^7$ ............................. A61K 7/48; A61K 7/50; A61K 31/74

(52) U.S. Cl. ................. 424/401; 424/78.02; 424/78.03; 424/78.07; 424/78.18; 424/405; 424/422.1; 514/772.3

(58) Field of Search ............................. 424/70.12, 401, 424/78.02, 78.03, 78.07, 78.18, 422.1, 405; 514/772.3

(56) References Cited

U.S. PATENT DOCUMENTS

| | | |
|---|---|---|
| 2,054,989 A | 9/1936 | Moore |
| 2,153,143 A | 4/1939 | Figg, Jr. et al. |
| 2,678,902 A | 5/1954 | Mehaffey |
| 3,131,152 A | 4/1964 | Klausner |
| 3,131,153 A | 4/1964 | Klausner |
| 3,395,214 A | 7/1968 | Mummert |
| 3,415,939 A | 12/1968 | Minton |
| 3,840,465 A | 10/1974 | Knowles et al. |
| 4,006,218 A | 2/1977 | Sipos |
| 4,199,564 A | 4/1980 | Silver et al. |
| 4,202,881 A | 5/1980 | Gross et al. |
| 4,254,104 A | 3/1981 | Suzuki |
| 4,464,293 A | 8/1984 | Dobrin |
| 4,478,853 A | 10/1984 | Chaussee |
| 4,501,834 A | 2/1985 | Su |
| 4,511,486 A | 4/1985 | Shah |
| 4,542,012 A | 9/1985 | Dell |
| 4,559,226 A | 12/1985 | Fogel et al. |
| 4,584,192 A | 4/1986 | Dell et al. |
| 4,671,957 A | 6/1987 | Holtshousen |
| 4,695,453 A | 9/1987 | Tuominen et al. |
| 4,719,239 A | 1/1988 | Muller et al. |
| 4,752,612 A | 6/1988 | Saito et al. |
| 4,806,262 A | 2/1989 | Snyder |
| 4,831,023 A | 5/1989 | Garlen et al. |
| 4,839,167 A | 6/1989 | Yamamoto et al. |
| 4,883,660 A | 11/1989 | Blackman et al. |
| 4,915,934 A | 4/1990 | Tomlinson |
| 4,931,282 A | 6/1990 | Asmus et al. |
| 4,956,170 A | 9/1990 | Lee |
| 4,957,908 A | 9/1990 | Nelson |
| 4,981,678 A | 1/1991 | Tomlinson |
| 5,120,716 A | 6/1992 | Miyazawa et al. |
| 5,128,123 A | 7/1992 | Brewster et al. |
| 5,149,719 A | 9/1992 | Ferber et al. |
| 5,164,107 A | 11/1992 | Khan et al. |
| 5,167,950 A | 12/1992 | Lins |
| 5,180,061 A | 1/1993 | Khan et al. |
| 5,180,584 A | 1/1993 | Sebag et al. |
| 5,223,261 A | 6/1993 | Nelson et al. |
| 5,225,473 A | 7/1993 | Duan |
| 5,232,691 A | 8/1993 | Lemole |
| 5,298,182 A | 3/1994 | Tsao et al. |
| 5,298,242 A | 3/1994 | Vanlerberghe et al. |
| 5,334,388 A | 8/1994 | Hoang et al. |
| 5,362,484 A | 11/1994 | Wood et al. |
| 5,409,966 A | 4/1995 | Duan et al. |
| 5,484,597 A | 1/1996 | Slavtcheff et al. |
| 5,512,199 A | 4/1996 | Khan et al. |
| 5,567,428 A | 10/1996 | Hughes |
| 5,585,092 A | 12/1996 | Trandai et al. |
| 5,626,853 A | 5/1997 | Bara et al. |
| 5,629,006 A | 5/1997 | Hoang et al. |
| 5,908,619 A | * 6/1999 | Scholz |
| 5,951,993 A | * 9/1999 | Scholz |
| 6,019,997 A | * 2/2000 | Scholz |
| 6,090,395 A | * 7/2000 | Asmus et al. ............... 424/401 |

FOREIGN PATENT DOCUMENTS

| | | |
|---|---|---|
| AU | B-72440/87 | 11/1987 |
| DE | 34 16 777 A1 | 11/1985 |

(List continued on next page.)

OTHER PUBLICATIONS

Guy et al., Selection of Drug Candidates for Transdermal Drug Delivery, *Transdermal Drug Delivery: Developmental Issues and Research Initiatives*; eds. Hadgraft and Guy, Marcel Dekker, Inc. (1989).

(List continued on next page.)

Primary Examiner—Thurman K. Page
Assistant Examiner—Humera N. Sheikh
(74) Attorney, Agent, or Firm—John A. Burtis

(57) ABSTRACT

A hydroalcoholic lotion is disclosed which comprises (a) a lower alcohol and water in a weight ratio of about 35:65 to 100:0, and (b) between at least 0.5% and 8% by weight thickener system comprised of at least one emulsifier present in at least 0.05% by weight wherein the composition in a polymer free state has a viscosity of at least 4,000 centipoise at 23 degrees C. and wherein the emulsifier is comprised of at least one hydrophobic group and at least one hydrophilic group. The hydroalcoholic composition is useful as a hand preparation such as a lotion or as a presurgical scrub replacement.

19 Claims, No Drawings

FOREIGN PATENT DOCUMENTS

| | | |
|---|---|---|
| DE | 36 32 030 A1 | 3/1988 |
| EP | 0 014 502 A1 | 8/1980 |
| EP | 0 223 681 A1 | 5/1987 |
| EP | 0 260 641 A2 | 3/1988 |
| EP | 0 289 160 A1 | 4/1988 |
| EP | 0 381 618 A1 | 8/1990 |
| EP | 0 451 949 A1 | 10/1991 |
| EP | 0 522 624 A1 | 1/1993 |
| EP | 0 689 767 A2 | 1/1996 |
| EP | 0 745 389 A1 | 12/1996 |
| FR | 788 811 | 10/1935 |
| FR | 77 31410 | 10/1977 |
| FR | 2 406 438 | 5/1979 |
| GB | 1 527 781 | 10/1978 |
| JP | 80 92 078 | 4/1996 |
| WO | 93/07903 | 4/1993 |
| WO | 94/13354 | 6/1994 |
| WO | 95/03772 | 2/1995 |
| WO | 97/00667 | 1/1997 |
| WO | WO 97/00668 | 1/1997 |
| WO | WO 97/48321 | 12/1997 |
| WO | WO 97/48322 | 12/1997 |

OTHER PUBLICATIONS

Smith et al., *Percutaneous Penetration Enhancers*; eds. Smith and Maibach (1995) (table of contents).

BIOSIS Abstract 80:188 400, Abstract of *Zentralbl Bakteriol Parasitenkd Infektionskr Hyg Erst Abt Orig Reihe B Hyg Krankaenhaushyg Betriebshyg Praev Med*, 168, pp. 5–6 (1979).

BIOSIS Abstract 86:434 601, Abstract of *Hyg. Med.*, 11, pp. 238–241 (1986).

Bulletin No. 51–0001–259, Speciality Chemicals of ICI America of Wilimington, DE.

J.L. Cohen et al., "Penetration of 5–Fluorouracil In Excised Skin", *The J. of Investigative Dermatology*, 62, pp. 507–509 (1974).

CTFA Cosmetic Ingredient Handbook, Published by The Cosmetic, Toiletry and Fragrance Association, Inc., pp. 37,64–65,78,81 (1988).

G.M. Eccleston, "Application of Emulsion Stability Theories to Mobile and Semisolid O/W Emulsions", *Cosmetics & Toiletries*, 101, pp. 73–92 (1986).

G.M. Eccleston, "Influence of long chain alcohols (or acids) and surfactants on the stabilities and consistencies of cosmetic lotions and creams", *Cosmetics and Toiletries*, 92, pp. 21–28 (1977).

E.D. Goodard et al., "Novel gelling structures based on polymer/surfactant systems", *J. Soc. Cosmet. Chem.*, 42, pp. 19–34 (1991).

P.B. Price, "Reevaluation Of Ethyl Alcohol As A Germicide", *Archives of Surgery*, pp. 492–502 (Undated).

R.B. Stoughton, "Vasoconstrictor Activity and Percutaneous Absorption of Glucocorticosteroids", *Arch. Derm.*, 99, pp. 753–756 (1969).

"Textbook of Polymer Science", F.W. Billmeyer, Ed.; Wiley–Interscience, NY; $2^{nd}$ Edition; pp. 84–85 (1971).

Yamashita et al., *Surfactants, Polymeric (Overview) in: Polymeric Materials Encyclopedia*, Salamone, J.C. Editor. CRC Press (1996) vol. 10, pp. 8195–8201.

* cited by examiner

STABLE HYDROALCOHOLIC COMPOSITIONS

This is a continuation of application Ser. No. 08/781,565 filed Jan. 9, 1997, now U.S. Pat. No. 6,090,395, which is a continuation-in-part of application Ser. No. 08/493,695, filed Jun. 22, 1995, now abandoned, both of which are incorporated herein by reference.

This application is a continuation-in-part of application Ser. No. 8/493,695, filed Jun. 22, 1995, abandoned incorporated herein by reference.

FIELD OF THE INVENTION

The present invention relates to compositions useful as skin disinfectants, surgical hand preparations, patient skin preparations and antimicrobial hand lotions. More specifically the invention relates to stable hydroalcoholic compositions which are thickened using emulsifier systems.

BACKGROUND OF THE INVENTION

Control of nosocomial infection and exposure to infectious disease is of paramount concern to doctors, nurses, and clinicians who work in hospitals and surgery centers. One of the most effective methods for controlling infection is regimented hand disinfection before and possibly after each patient contact and particularly before and after each surgical procedure. Hand disinfection is generally accomplished using antimicrobial soaps with water. These soaps are usually formulated to include either povidone-iodine (usually 10% by weight) or chlorhexidine gluconate (CHG) (usually 2 or 4% by weight) as the active antimicrobial agent. In addition, these formulated soaps may contain surfactants and possibly low levels of humectants such as glycerin.

Hand disinfection is also accomplished using presurgical scrub replacements. These are used instead of the soap and water scrub. Presurgical scrub replacements ideally achieve bacterial kill equal to or better than a traditional soap and water scrub and in a shorter period of time. Additionally, they maintain or improve the skin's natural barrier to microbial and chemical contamination while providing acceptable tactile properties. Examples of presurgical scrub replacements include hydroalcoholic gels which generally include high levels of either ethanol or isopropanol as the disinfecting agent and also include a thickener and optionally include a humectant (e.g. glycerin). To date, thickeners used in hydroalcoholic gels have been based on anionic polymers such as polyacrylic acid (sold under the tradename Carbopol by BF Goodrich Specialty Polymers and Chemicals Division of Cleveland, Ohio). U.S. Pat. No. 4,915,934 to Tomlinson discloses the use of CHG-containing antiseptic foams based on hydroalcoholic solvents, a fatty alcohol, and a surfactant. The surfactant is selected from the group of ethoxylated sorbitan alkylates, ethoxylated fatty alcohols, and ethoxylated nonyl phenols.

Formulating stable viscous hydroalcoholic emulsions is difficult for two reasons. First, addition of short chain alcohols (such as ethanol) to an aqueous system decreases the surface tension dramatically. For example, 40% by weight ethanol in water has a surface tension of approximately 31 dyne/cm compared to pure water which has a surface tension of about 72 dyne/cm at 20° C. A hydroalcoholic solution at 60% by weight ethanol has a dramatically decreased surface tension as compared to water. Such a composition has a surface tension of approximately 27 dyne/cm at 20° C. Second, many surfactants typically used in cosmetic emulsions become completely or partially soluble in hydroalcoholic systems.

In bulletin 51-0001-259 regarding skin care, Specialty Chemicals of ICI Americas of Wilmington, Del. stated that although ethanol can provide several benefits to skin care emulsions, formulations often avoid ethanol as it is difficult to prepare stable emulsions in its presence. In fact, the bulletin continued that ethanol is often used to break emulsions.

U.S. Pat. No. 4,956,170 to Lee discloses a hydroalcoholic skin moisturizing/conditioning antimicrobial gel. The gel comprises 60–75% ethanol and 0.4–2% of a polymeric thickening agent. The formulations also comprise polyethoxylated non-ionic surfactants/emulsifiers to stabilize the added emollient oils in addition to a fatty alcohol.

U.S. Pat. No. 5,167,950 to Lins discloses an antimicrobial aerosol mousse having a high alcohol content. The mousse comprises alcohol, water, a polymeric agent and a surfactant system uprising a C16–C22 alcohol, aerosol propellant and a non-ionic polyethoxylated surfactant.

SUMMARY OF THE INVENTION

The present invention provides compositions useful as products for skin disinfection such as presurgical hand preps, patient preps, and lotions. The preferred formulations of the present invention, in general, have a very nice feel after both single and multiple applications. Additionally, preferred formulations maintain or improve the skin condition after multiple applications and no slimy or abnormal feeling is noticeable during post application hand washing. When used as a presurgical scrub replacement, the present invention achieves bacterial, fungal, and viral kill equal to or better than a traditional soap and water scrub in a shorter period of time while maintaining or improving the skin's natural barrier to microbial and chemical. The invention overcomes the shortcomings of past compositions by providing a viscous composition which includes a high concentration of a lower alcohol but does not require a polymeric thickener to make the composition viscous.

This invention provides a hydroalcoholic lotion comprised of (a) a lower alcohol and water in a weight ratio of about 35:65 to 100:0, and (b) between at least 0.5% and 8% by weight thickener system comprised of at least one emulsifier present in at least 0.05% by weight wherein the composition in a polymer free state has a viscosity of at least 4,000 centipoise at 23 degrees C. and wherein the emulsifier is comprised of at least one hydrophobic group and at least one hydrophilic group, wherein: (i) the hydrophobic group is comprised of an alkyl group of at least 16 carbon atoms; an alkenyl group of at least 16 carbon atoms; or an aralkyl or an aralkenyl group of at least 20 carbon atoms; and (ii) the hydrophilic group is comprised of ethylene oxide/propylene oxide copolymers having 2–150 moles of ethylene oxide plus propylene oxide per mole of hydrophobe bonded to the hydrophobe through an ether or ester bond and optionally terminated by an alkyl or alkenyl group of 1 to 36 carbon atoms or an aralkyl of between 6 and 36 carbon atoms.

This invention further provides a hydroalcoholic lotion comprised of (a) a lower alcohol and water in a weight ratio of about 35:65 to 100:0, (b) between at least 0.5% and 8% by weight thickener system comprised of at least one emulsifier present in at least 0.05% by weight wherein the emulsifier is comprised of at least one hydrophobic group and at least one hydrophilic group, wherein: (i) the hydrophobic group comprising at least 16 carbon atoms; an alkenyl group of at least 16 carbon atoms; or an aralkyl or an aralkenyl group of at least 20 carbon atoms; and (ii) the hydrophilic group is comprised ethylene oxide/propylene oxide copolymers having 2–150 moles of ethylene oxide plus propylene oxide per mole of hydrophobe and bonded to the hydrophobe through an ether or ester bond and optionally terminated by an alkyl or alkenyl group of 1 to 36 carbon atoms or an aralkyl group of between 6 and 36 carbon atoms, alcohol; esters and ethers of polyhydric alcohols and their polyalkoxylated derivatives; esters and ethers of sorbitan and polyalkyleneoxide derivatives of sorbitan having 2–150 moles of alkylene oxide units per mole of hydrophobe; as well as combinations of these groups, and (c) the thickener system has a hydrophobe number average chain length greater than 22 carbon atoms and provides a composition in a polymer free state with a viscosity of at least 4,000 centipoise at 23 degrees C.

The invention also provides a hydroalcoholic lotion comprised of (a) a lower alcohol and water in a weight ratio of about 35:65 to 100:0, (b) between at least 0.5% and 8% by weight thickener system comprised of at least two emulsifiers where each emulsifier is present in at least 0.05% by weight where the emulsifiers are comprised of at least one hydrophobic group and one hydrophilic group, wherein: (i) the hydrophobic group is comprised of an alkyl group of at least 16 carbon atoms; an alkenyl group of at least 16 carbon atoms; or an aralkyl or an aralkenyl group of at least 20 carbon atoms; and (ii) the hydrophilic group is comprised ethylene oxide/propylene oxide copolymers having 2–150 moles of ethylene oxide plus propylene oxide mole of hydrophobe and bonded to the hydrophobe through an ether or ester bond and optionally terminated by an alkyl or alkenyl group of 1 to 36 carbon atoms or an aralkyl group of between 6 and 36 carbon atoms, alcohol; esters and ethers of polyhydric alcohols and their polyalkoxylated derivatives; esters and ethers of sorbitan and polyalkyleneoxide derivatives of sorbitan having 2–150 moles of alkylene oxide units per mole of hydrophobe; as well as combinations of these groups, and (c) in a polymer free state the composition has a viscosity of at least 4,000 centipoise at 23 degrees C.

The invention provides a hydroalcoholic composition comprised of (a) a lower alcohol and water in a weight ratio of about 35:65 to 100:0, (b) between at least 0.5% and 8% by weight thickener system comprised of at least one emulsifier present in at least 0.05% by weight wherein the emulsifier is comprised of at least one hydrophobic group and at least one hydrophilic group, wherein: (i) the hydrophobic group is comprised of an alkyl group of at least 16 carbon atoms; alkenyl group of at least 16 carbon atoms; or an aralkyl or an aralkenyl group of at least 20 carbon atoms; and (ii) the hydrophilic group is comprised ethylene oxide/ propylene oxide copolymers having 2–150 moles of ethylene oxide plus propylene oxide mole of hydrophobe and bonded to the hydrophobe through an ether or ester bond and optionally terminated by an alkyl or alkenyl group of 1 to 36 carbon atoms or an aralkyl group of between 6 and 36 carbon atoms, alcohol; esters and ethers of polyhydric alcohols and their polyalkoxylated derivatives; esters and ethers of sorbitan and polyalkyleneoxide derivatives of sorbitan having 2–150 moles of alkylene oxide units per mole of hydrophobe; as well as combinations of these groups, and (c) in a polymer free state the composition has a viscosity of at lest 45,000 centipoise after 19 days at 23 degrees C.

A method of preparing a stable hydroalcoholic composition is further provided. The method comprises steps of (a) preparing a thickener system comprised of at least one emulsifier, the emulsifier present in at least 0.05% by weight in the composition to provide 4,000 centipoise at 23 degrees when the composition is free of auxiliary thickeners, wherein the emulsifier is comprised of at least one hydrophobic group and at least one hydrophilic group, wherein: (i) the hydrophobic group is comprised of an alkyl group of at least 16 carbon atoms; alkenyl group of at least 16 carbon atoms; or an aralkyl or aralkenyl group of at least 20 carbon atoms; and (ii) the hydrophilic group is comprised ethylene oxide/propylene oxide copolymers having 2–150 moles of ethylene oxide plus propylene oxide per mole of hydrophobe and bonded to the hydrophobe through an ether or ester bond and optionally terminated by an alkyl or alkenyl group of 1 to 36 carbon atoms or an aralkyl group of between 6 and 36 carbon atoms, alcohol; esters and ethers of polyhydric alcohols and their polyalkoxylated derivatives; esters and ethers of sorbitan and polyalkyleneoxide derivatives of sorbitan having 2–150 moles of alkylene oxide units per mole of hydrophobe; as well as combinations of these groups, and (b) combining the thickener system and a hydroalcoholic solvent at a temperature sufficient to melt the thickener system wherein the hydroalcoholic solvent is comprised of a lower alcohol and water in a weight ratio of about 35:65 to 100:0.

A further method of preparing a stable hydroalcoholic composition is provided comprising the steps of (a) heating a thickener system comprised of at least one emulsifier, the emulsifier present in at least 0.05% by weight in the composition wherein the composition free of auxiliary thickeners has a viscosity of at least 4,000 centipoise at 23 degrees C. and wherein the emulsifiers have at least one hydrophobic group and at least one hydrophilic group, wherein: (i) the hydrophobic group is comprised of an alkyl group of at least 16 carbon atoms; an alkenyl group of at least 16 carbon atoms; or an aralkyl or an aralkenyl group of at least 20 carbon atoms; and (ii) the hydrophilic group is comprised ethylene oxide/propylene oxide copolymers having 2–150 moles of ethylene oxide plus propylene oxide per mole of hydrophobe and bonded to the hydrophobe through an ether or ester bond and optionally terminated by an alkyl or alkenyl group of 1 to 36 carbon atoms or an aralkyl group of between 6 and 36 carbon atoms, alcohol; esters and ethers of polyhydric alcohols and their polyalkoxylated derivatives; esters and ethers of sorbitan and polyalkyleneoxide derivatives of sorbitan having 2–150 moles of alkylene oxide units per mole of hydrophobe; as well as combinations of these groups, and (b) heating the thickener system to a temperature sufficient to melt the thickener system, (c) heating an aqueous solution to a temperature above its melt temperature, (d) combining the thickener system and the aqueous solution, and (e) adding a lower alcohol to the combination wherein the alcohol to water ratio in the composition is between about 35:65 to 100:0 by weight.

DEFINITIONS

"Ambient temperature" as used herein refers to the temperature range between about 21 and 25 degrees C.

"Auxiliary thickeners" as used herein refers to additives (other than the thickener system described below) which increase the viscosity of the solvent phase even in the absence of the thickener system. Certain auxiliary thickeners may act synergistically with the thickener system to increase the viscosity of the resultant formula. Auxiliary thickeners include but are not limited to soluble and swellable polymers and associative colloidal thickeners such as silica, magnesium aluminum silicate and the like.

"Emollient" as used herein refers broadly to materials which are capable of maintaining or improving the moisture level, compliance, or appearance of the skin when used repeatedly.

"Polymer" as used herein refers to a natural or synthetic molecule having repetitive units and a number average molecular weight of at least 20,000.

"Emulsifier" as used herein is synonymous with "surfactant" and refers to molecules comprising hydrophilic (polar) and hydrophobic (non-polar) regions on the same molecule.

"Emulsion" as used herein refers to a stable dispersion of one liquid in a second immiscible liquid.

"Lotion" means liquid or cream, free of any propellant.

"Melt temperature" (Tm) as used herein refers to the temperature at which compositions or emulsions of the present invention dramatically lose viscosity.

"Solvent", "solvent system" or "hydroalcoholic solvent" as used herein refer to the alcohol and water combination in the present invention.

"Stable" as used herein refers to a composition that displays less than or equal to 10% by volume separation after standing for 6 months at ambient temperature or after centrifuging at 2275×g for 30 minutes at ambient temperature.

"Surfactant" as used herein is synonymous with "emulsifier," the definition of which is given above.

"Thickener system" as used herein refers to a single emulsifier or a combination of emulsifiers wherein each emulsifier is present in a concentration of at least 0.05% by weight capable of providing a viscosity of at least 4,000 centipoise without auxiliary thickeners at 23° C. to the compositions of the present invention.

DETAILED DESCRIPTION OF THE INVENTION

The invention provides a composition comprised of a lower hydrocarbon chain alcohol, water, and thickening system. Alcohols used in the present invention are first discussed followed by a discussion of thickening systems. Ingredients which are optionally added to the composition such as antimicrobial agents and emollients are then discussed followed by a discussion of how to prepare compositions of the present invention. A related patent application entitled. "Stable Hydroalcoholic Compositions," Ser. No. 08/493,714 filed on Jun. 22, 1995 by inventors Scholz, Asmus and Charpentier is hereby incorporated by reference.

Alcohol

The alcohol used in the present invention is a lower hydrocarbon chain alcohol such as a C1–C4 alcohol. In preferred embodiments the alcohol is chosen from ethanol, 2-propanol, or n-propanol, and most preferably ethanol. Ethanol is a preferred alcohol since it provides broad spectrum and quick killing of microbes and has an odor acceptable to consumers such as doctors, nurses and clinicians. The invention anticipates that a single alcohol may be used or that a blend of two or more alcohols may comprise the alcohol content of the composition.

The alcohol to water ratio in the present invention is between about 35:65 and 100:0 by weight. Compositions having alcohol to water ratios within the range 40:60 to 95:5 ensure an efficacious immediate bacterial kill. In a preferred embodiment the alcohol:water ratio is between about 50:50 and 85:15, more preferably between about 60:40 and about 75:25, and most preferably the alcohol:water ratio is between about 64:36 and 72:28 by weight. Higher alcohol to water ratios are used in a preferred embodiment for optimum antimicrobial activity and to ensure the composition is fast drying.

Thickener System

The thickener system useful in this invention affects the cosmetic attributes of the final composition. Preferably, hand preps and lotions of the invention have the following desirable cosmetic attributes. The composition should not result in excessive clumping of glove powder beneath powdered surgical gloves and should not affect the integrity of the glove material. The composition should maintain an acceptable viscosity at 25° C. and preferably up to 35° C. Finally, in the most preferred embodiments formulations are stable to heat and cool cycles (heating up to 50° C. or higher and cooling back to ambient temperature) as well as freeze/thaw cycles (cooling to −30° C. and warming to ambient temperature). All of these cosmetic attributes are affected by the types and amounts of emulsifiers chosen which comprise the thickener system of the present invention and are discussed below.

The thickener system of the invention must be compatible with the hydroalcoholic solvent system described above in order to provide acceptable cosmetic properties and appropriate viscosity. Compositions of this invention have a viscosity of at least about 4,000 cps at 23° C., preferably at least about 10,000 cps, more preferably at least about 20,000, even more preferably at least about 50,000 cps, even more preferably at least about 100,000 cps, and most preferably about 80,000 to about 500,000 cps measured using a very low shear viscometer such as Brookfield LVDV-I$^+$ viscometer and T spindles with a heliopath adapter. Since the emollient system and other optional ingredients may affect the viscosity (either positively or negatively), the measured viscosity is that of the final composition without any added auxiliary thickeners.

The viscosity of the present invention is imparted by an thickner system comprising at least one emulsifier, and preferably at least two emulsifiers, and more preferably at least two emulsifiers from different classes. In certain embodiments of the present invention, the emulsifier system can include only one commercially available emulsifier (which will typically be a mixture of emulsifiers). At least one of the emulsifiers is preferably a solid at room temperature comprising at least one long chain hydrocarbon of at least 16 carbon atoms, preferably at least 18 carbon atoms, and more preferably at least 22 carbon atoms and at lower alcohol:water ratios of greater than 60:40 the long chain hydrocarbon preferably has greater than 22 carbon atoms. The thickener system of the present invention can be described in terms of the number average chain length, and preferably has a hydrophobe number average chain length of greater than about 22 carbon atoms. "Emulsifiers" of this invention refers to compounds comprising hydrophilic (polar) and hydrophobic (non-polar) regions on the same molecule and conform to the general structure:

Where "R" represents a hydrophobic group and L represents a hydrophilic group. Where "a" and "b" are independently 1 to 4.

In this invention "R" comprises an alkyl group of at least 16 or 18 carbon atoms, preferably at least 20 carbon atoms and more preferably at least 22 carbon atoms, and most preferably at least 24 carbon atoms; alkenyl group of at least 16 or 18 carbon atoms, preferably at least 20 carbon atoms and more preferably at least 22 carbon atoms, and most preferably at least 24 carbon atoms; aralkyl or aralkenyl group of at least 20 carbon atoms, preferably at least 24 carbon atoms and more preferably at least 26 carbon atoms. In a preferred embodiment R is unbranched.

In the above formula, "L" is comprised of ethylene oxide and/or propylene oxide group, preferably having 2–150 moles of ethylene oxide plus propylene oxide per mole of hydrophobe which is bonded to the hydrophobe through an ether or ester bond and optionally terminated by C1–C36 alkyl ester, C2–C36 alkenyl ester or C6–C36 alkaryl ester; (i.e., aralkyl ester) alcohol, polyhydric alcohols such as, but not limited to, ethylene glycol, propylene glycol, butylene glycol, pentaerythrytol, glycerol, and sorbitol esters and ethers of polyhydric alcohols and their polyalkoxylated derivatives; ethers and esters of sorbitan or polyalkoxylated (i.e., polyalkyleneoxide) derivatives of sorbitan having 2–150 moles of alkylene oxide units per mole of hydrophobe; as well as combinations of these groups.

The hydrophobic and hydrophilic groups are generally selected to have a hydrophile/lipophile balance (HLB) of about 2 to about 20 and preferably about 4 to about 16 and more preferably about 8 to about 12. Furthermore, the weight average HLB of the thickener system is preferably about 4 to about 16 and more preferably about 8 to about 12. For example, a thickener system of 40% by weight of an emulsifier having an HLB of 10 and 60% of an emulsifier having an HLB of 15 has a HLB of 13.

The emulsifier(s) which comprise thickener systems may be chosen from a single class of surfactants (e.g., a mixture of chain length polyethoxylated alcohols) but is preferably a mixture of emulsifier classes. Many commercially available emulsifiers are actually comprised of a mixture of chain lengths. For example, some behenyl alcohol as commercially supplied is actually a mixture of alcohols consisting of primarily C22 and C20 fractions but contain detectable levels of C24, C18 and C16 fractions. For this reason, the chain lengths specified herein refer to the number average chain length. Furthermore, for the multiple emulsifier compositions of the present invention, each emulsifier must be present in a concentration of at least about 0.05% and more preferably at least about 0.1% by weight to be considered a component of a thickener system. Thickener systems of the present invention are capable of achieving high viscosities at relatively low total emulsifier concentrations. The total concentration of emulsifiers present as a thickener system is generally less than about 8% by weight, more preferably less than about 5% by weight more preferably less than about 4% by weight and most preferably less than about 3% by weight of the total composition of the present invention. Typically, the thickener system is present in the composition in an amount of at least about 0.5% by weight, based on the total weight of the composition. In the most preferred compositions of this invention, the thickener system comprises between about 0.75% by weight to about 5% by weight, more preferably between about 1.0% by weight to about 3.5% by weight and most preferably between about 1.5% by weight to about 3% by weight of the composition. As used herein an emulsifier is considered part of the thickener system if its presence in the formula results in an increase in the viscosity of the composition. If a certain emulsifier does not result in increasing the viscosity of the composition, it is considered an emollient or stabilizer as defined below.

Preferred compositions of the present invention which are substantially free of polymeric thickening agents of the present invention have a "melt temperature" (Tm). If compositions are heated above this melt temperature, they dramatically lose viscosity. The compositions of the present invention preferably have melt temperatures greater than 25° C. in order to maintain a high viscosity at room temperature. More preferably the melt temperature is greater than 35° C. in order to maintain viscosity once applied to the skin. The most preferred formulations have a melt temperature greater than 40° C. in order to allow shipping and handling without refrigeration. Thickener systems affect the melt temperature of a given composition. In order to obtain a preferred melt temperature a preferred thickener system includes at least one emulsifier which is solid at ambient temperature. Preferably, all emulsifiers of a thickener system are solid at ambient temperature to increase the melt temperature of the resultant composition.

The structure of emulsifiers in a thickener system affects the melt temperature of the resultant composition. In a preferred embodiment at least one emulsifier in a thickener system is capable of promoting a crystalline structure. Crystallinity is promoted by long straight chain alkyl groups, therefore, at least one emulsifier preferably comprises a saturated straight chain hydrocarbon of at least 16, preferably at least 18 and most preferably at least 20 carbon atoms. Certain hydrophilic head groups have been found to particularly promote association and crystallization. Suitable crystalline emulsifiers include: alkyl alcohols and alkyl esters of polyethylene glycol.

In addition to affecting the melt temperature of a composition, the emulsifier chain length also helps to determine the maximum level of ethanol which can be used in the composition and the concentration of emulsifiers required in the thickener system. At higher levels of alcohol, longer chain emulsifiers are required to produce viscous stable emulsions. It is believed that higher levels of alcohol tend to swell or solubilize the emulsifiers to a greater degree than lower levels of alcohol. Therefore, as the concentration of ethanol increases the chain length of the hydrocarbon chains in a thickening system must also increase in order to maintain a melt temperature over 35° C. That is, the amount of lower alcohol in the hydroalcoholic system can affect the choice of surfactant, (i.e., emulsifier) and vice versa. For example, if the composition includes a lower alcohol to water ratio in excess of about 50:50, the thickener system should include at least one surfactant having a number average chain length of at least 16 carbon atoms. If the composition includes a lower alcohol to water ratio in excess of about 60:40, the thickener system should include at least one surfactant having a number average chain length of at least 18 carbon atoms. If the composition includes a lower alcohol to water ratio in excess of about 64:36, the thickener system should include at least one surfactant having a number average chain length of at least 20 carbon atoms.

For example, a thickener system based on a steareth-2 emulsifier in 60:40 ethanol:water ratio produces a stable composition with a viscosity of about 63,000 cps at ambient temperature. The same thickener system with an ethanol to water ratio of 66:34 did not produce a stable composition. An analogous system in 60:40 ethanol:water ratio having C22 hydrocarbon chain have viscosities of about 5,000 cps.

The nature and size of hydrophilic head groups of emulsifiers are important and help to determine which thickening systems produce viscous stable systems. Certain combinations of emulsifiers will produce viscous stable emulsions. Without being bound by theory, it is believed that the size, charge, and degree of hydrogen bonding are important parameters to determine how emulsifiers interact.

Many preferred thickener systems are capable of producing viscoelastic compositions which are very stable. By varying the ratio of emulsifiers, the degree of elasticity can be adjusted from almost a purely viscous composition to a highly elastic and even stringy composition. If emollients are added, increasing the elasticity of the system imparts added stability to prevent separation of immiscible emollients. Excessive elasticity, however, is not preferred since an elastic composition usually does not provide a cosmetically appealing product. Adding certain emulsifiers with at least two hydrophobic components has been shown to limit the viscoelasticity while ensuring viscous stable compositions. A favored class of multiple hydrophobic component emulsifiers are quaternary ammonium salts conforming substantially to the following structure:

$$R'-\underset{\underset{R''''}{|}}{\overset{\overset{R'''}{|}}{N}}-R'' \quad X^-$$

where:

R' and R'' are long chain alkyl or alkenyl hydrocarbon chains of at least 16 carbon atoms;

R''' is a short chain alkyl group of 1 to 4 carbon atoms, preferably methyl or ethyl;

R'''' is equivalent to either R' or R''' and is preferably equivalent to R''', and X is a halogen, $R'''SO_3^-$, $R'''SO_4^-$, or $R'''CO_2^-$.

Some preferred structures include distearyldimethylammonium chloride, dibehenyldimethylammonium chloride, and dibehenyldimethylammonium methosulfate, while dibehenyldimethylammonium methosulfate is a more preferred structure. Other suitable multiple hydrophobic emulsifiers include dialkylglycerol esters, polyglycerol alkyl esters, ethylene glycol dialkylesters, polyethylene glycol dialkylesters, dialkylamides of diamines such as ethylene diamine, polyalkylesters of pentaerythrityl and dialkyl (optionally ethoxylated) phosphates, and alkyl esters of polyethyoxylated alkyl alcohols.

The following emulsifier classes are offered as nonlimiting examples of suitable emulsifiers for use in the present invention. Examples of some preferred emulsifiers are provided for each emulsifier class.

Class 1. Polyethoxylated and/or Polypropoxylated Alcohols and Esters and Derivatives Thereof $$R_6(C(O))_pO(CH_2CH_2O)_m(CH_2CHO)_rR_t \quad | \quad CH_3$$

where $R_6$ is a straight or branched chain alkyl or alkenyl hydrocarbon chain of at least 16 carbon atoms, preferably at least 18, more preferably at least 20 carbon atoms, and most preferably at least 22 carbon atoms optionally substituted in available positions by N, O, and S, or an aralkyl group of 16 to 36 carbon atoms; m=0–200, preferably 2–50, most preferably 4–20; and p=0 or 1;

$$R_8 = H \quad or \quad -\overset{\overset{O}{\|}}{C}-R_{12};$$

$R_{12}$ is an alkyl or alkenyl group of 1 to 36 carbon atom(s) optionally substituted in available positions by N, O, and S, or an aralky group of 6 to 36 carbon atoms; and r=0–50.

Some examples of preferred emulsifiers from the class of polyethoxylated alcohols and esters include but are not limited to steareth-2 available as "BRIJ 72" from ICI Americas Inc. of Wilmington, Del.; steareth-10 available as "BRIJ 76" from ICI; beheneth-5 available as "NIKKOL BB-5" from Barnet Products Inc.; beheneth-10 available as "NIKKOL BB-10" from Barnet; C31 alkyl-10EO available as "UNITHOX 450" from Petrolite Corp. of Tulsa, Okla.; and C31 alkyl-40 EO available as "UNITHOX 480" from Petrolite.

Class 2. Alkyl and Alkenyl Alcohols $$R_6-OH$$

where $R_6$ is as defined above in Emulsifier Class 1.

Nonlimiting examples of preferred alkyl and alkenyl alcohol emulsifiers useful in a thickener system of the invention include stearyl alcohol available as "LANETTE 18" from Henkel's Emery Division of Cincinnati, Ohio; behenyl alcohol available as "LANNETTE 22" from Henkel; oleyl alcohol available as Novol from Croda; C-24 alcohol available as "UNILIN 350" from Petrolite of Tulsa, Okla.; C31 alcohol available as "UNILIN 425" from Petrolite; and arachidyl alcohol available as "AR-20" from M Michel and Co. of New York, N.Y.

Class 3. Esters and Ethers of Polyhydric Alcohols $$HO(CH_2\underset{\underset{R_9}{|}}{\overset{\overset{R_9}{|}}{C}})(\overset{\overset{R_9}{|}}{CH})_tO(\overset{\overset{O}{\|}}{C})_s-R_{12}$$

where t=0–4; each $R_9$ is independently chosen from H, —OH, —$CH_2OR_{10}$, or hydrocarbon chain of 1 to 4 carbon atoms, preferably C1; s=0 or 1; $R_{10}$=H or $R_{12}$ as described above in Class 1.

Examples of esters and ethers include glycerol monobehenate, pentaerythritol)distearate and glycerol tribehenate.

Esters and ethers of polyethoxylated polyhydric alcohols are also useful. For example, these include but are not limited to polyethoxylated glycerol monostearate, polyethoxylated pentaerythritol behenate, polyethoxylated propylene glycol monostearate.

Class 4. Sorbitan Fatty Acid Esters $$R_7(OCH_2CH_2)_vO \underset{O}{\overset{}{\diagup\diagdown}} O(CH_2CH_2O)_vR_7$$
$$CH-O(CH_2CH_2O)_vR_7$$
$$CH_2O(CH_2CH_2)_vC-R_6$$
$$\|$$
$$O$$

where $R_7$ is $$-\overset{\overset{O}{\|}}{C}R_6 \quad or \quad -H,$$

each v is independently 0–30; and $R_6$ is as defined above.

Fatty acid esters of sorbitan and its polyethoxylated derivatives are also examples of additional emulsifiers useful in the present invention.

Certain combinations of the above-listed emulsifiers are useful in some preferred embodiments to form viscous stable thickener systems of the present invention. These preferred systems are listed below.

Nonlimiting Examples of Suitable Thickener Systems:

| System # | Emulsifier 1/(class*) | Emulsifier 2/(class*) | Emulsifier 3 |
|---|---|---|---|
| 1 | polyethoxylated alcohol (1) | alkyl alcohol (2) | |
| 2 | polyethoxylated alkyl alcohol (1) | | |
| 3 | polyethoxylated alcohol C-30 (1) | alkyl alcohol (2) | |
| 4 | polyethoxylated alcohol (1) | alkyl alcohol C-24 (2) | |
| 5 | polyhydric alcohol ester (3) | ethoxylated alkyl alcohol (1) | |
| 6 | alkyl ester of sorbitan (4) | polyethoxylated alcohol (1) | |
| 7 | alkyl alcohol (2) | alkyl ester of a polyethoxylated alcohol (1) | |
| 8 | polyethoxylated alkyl alcohol (1) | alkyl ester of a polyethoxylated alcohol (1) | |
| 9 | alkyl alcohol (2) | polyethoxylated alkyl alcohol (1) | dimethicone copolyolalkyl phosphate |
| 10 | polyglycerol ester | polyethoxylated alcohol (1) | alkyl alcohol (2) |
| 11 | polyethoxylated alcohol (1) | alkyl alcohol (2) | quaternary amine |

*Refers to Emulsifier Class Number identified above

It is a simple matter to test certain combinations of emulsifiers to determine if they provide a suitable thickener system. Screening methodology is set forth in the Examples. The examples illustrate the importance of the head group size with respect to the ratio of the mixed emulsifiers required to produce a stable emulsion.

Without intending to be bound by theory, the physical structure of the composition of the invention is believed to be that of an emulsion. A classic definition of an emulsion is a stable dispersion of one liquid in a second immiscible liquid. However, as stated earlier, the present composition is preferably formed using at least one emulsifier which is a wax at room temperature. Although compositions of the present invention are not well characterized, they are believed to be viscous stable mixtures of a solid, semisolid, or liquid phase in a second liquid phase. It is believed that if certain hydrophobic emollients are added to the present invention, hydrophobic emulsifiers and immiscible emollients form an "oil" or hydrophobic phase which is dispersed in the hydroalcoholic liquid phase to form an "oil" in "water" emulsion. The hydroalcoholic phase is referred to herein as the "water" phase. Since many preferred emulsions are somewhat viscoelastic, these emulsions are believed to be liquid crystalline emulsions which have been cooled below the crystallization temperatures of the chosen emulsifiers to form a semi-crystalline gel-like network. Certain formulations may be simply swollen crystalline precipitates forming a strongly interacting network in the hydroalcoholic phase (so called coagel phase). The compositions of the present invention may also exist as combinations of these structures. Liquid crystalline and coagel phases in aqueous systems are described in "Application of Emulsion Stability Theories to Mobile and Semisolid O/W Emulsions," *Cosmetics and Toiletries*, Vol. 101, pp 73–92 (1986), and "Influence of Long Chain Alcohols (or Acids) and Surfactants on the Stability and Consistencies of Cosmetic Lotions and Creams," *Cosmetics and Toiletries*, Vol. 92, pp. 21–28 (1977) both of which are hereby incorporated by reference. The exact type of molecular association that occurs depends on many factors including the nature, size, and physical and chemical states of the polar and hydrocarbon portions of the emulsifiers which comprise the thickener system at a specified temperature.

Emulsifiers other than those required in the composition to provide a thickener system may also be added as emollients or stabilizers. For example, certain emollients are also comprised of hydrophobic and hydrophilic regions and are useful in the present invention since they are believed to become incorporated into the liquid crystalline network. These emulsifiers tend to enhance the stability of the composition as is discussed more fully below. Furthermore, certain dimethicone copolyol surfactants can actually improve the stability of formulations incorporating emollients. This is also discussed in more detail below.

Optional Ingredients

In addition to alcohol, water and thickener system, the compositions of the present invention may optionally include ingredients such as salts, emollients, stabilizers, antimicrobials, fragrances, therapeutic agents, propellants and additional emulsifiers. Each of these optional ingredients along with the effect each has upon the properties of the final composition is discussed below.

Salts

The melt temperature of the compositions of the present invention may be increased by adding salts. As the concentration of salt is increased, the ratio of emulsifiers will often need to change in order to maintain a stable composition. It is important to choose salts which do not create an unstable system and are compatible with any antimicrobials present in the system. For example, chlorhexidine digluconate (CHG) will precipitate rapidly in the presence of halide salts above a concentration of about 0.1 M. Therefore, if a system includes CHG, preferably gluconate salts such as triethanolamine gluconate or sodium gluconate are used.

Stabilizers

A stable composition is one which does not separate more than 10% by volume after centrifuging at 2275×g measured at the longitudinal midpoint of the sample tube for 30 minutes. It is also recognized that stability may be time dependent due to crystallization of emulsifiers and/or emollients present in the system, coalescence of emollients, emulsifiers and the like and, therefore preferred compositions do not exhibit separation of more than 10% after standing for six months at ambient conditions. Two types of stabilizers are useful in the present invention. These include (1) those stabilizers that complex with emulsifier hydrophilic head groups, and (2) those that associate with the emulsifier hydrophobic tails. Certain stabilizers may perform both functions. For example, emulsifiers comprising hydroxyl-containing head groups such as alkylpolyglucosides, monoalkylglycerides, and polyglycerol alkyl esters, may be "stabilized" by adding borate ion. Without intending to be bound by theory, it is believed that borate ions complex with adjacent head groups which may increase the association of hydrophobic tails by holding them in close proximity. Natural or synthetic polymers comprised of pendent long chain alkyl groups (greater than 12 and preferably greater than 16 carbon atoms) such as stearyl modified cellulose derivatives, stearyl modified proteins such as wheat protein, stearyl modified collagen and the like are capable of stabilizing compositions of the present invention. Such added components may also increase the melt temperature of compositions of the present invention. It is believed that the pendent alkyl groups in these polymers associate by Van der Waals interactions with the hydrophobes of a thickening system, thereby enhancing the stability of the crystalline structure. Polymeric thickeners which do not have associative pendent alkyl chains may also increase the melt temperature presumably by increasing the viscosity of the continuous phase. A nonlimiting example of such thickeners are quaternary celluloses such as Celquat™ 230M as available from National Starch of Bridgewater, N.J. In a preferred embodiment stearyldimonium hydroxypropyl cellulose commercially available as Crodacel QS from Croda Inc., Parsippany, N.J. is added as a stabilizer.

Emollients

Emollients are typically added to hand lotions or hand preps because they act to increase the moisture content of the stratum corneum. Emollients are generally separated into two broad classes based on their function. The first class of emollients function by forming an occlusive barrier to prevent water evaporation from the stratum corneum. The second class of emollients penetrate into the stratum corneum and physically bind water to prevent evaporation. The first class of emollients is subdivided into compounds which are waxes at room temperature and compounds which are liquid oils. The second class of emollients includes those which are water soluble and are often referred to as humectants.

For the purposes of this invention the thickener system is considered separate and distinct from any emollients which may be added even though it is recognized that the emulsifiers may function as occlusive emollients and aid in maintaining or improving the skin condition. Emollients are included in a preferred embodiment of the invention and preferably comprise between about 3 and 30%, more preferably between about 4 and 20% and most preferably between about 5 and 12% by weight of the formulation.

The ratio of wax to liquid emollients (oils and humectants) in a preferred embodiment of this invention is between about 5:1 to 1:5 and more preferably between about 1:3 to 3:1. Also, the ratio of wax emollients and wax emulsifiers to liquid emollients and liquid emulsifiers in a preferred embodiment of this invention is from about 1:5 to about 5:1, and more preferably, from about 1:3 to about 3:1. Emollients may be selected from any of the classes known in the art. A general list of useful emollients appears in U.S. Pat. No. 4,478,853 and EPO patent application 0 522 624 A1 and in the *CTFA Cosmetic Ingredient Handbook* published by The Cosmetic, Toiletry, and Fragrance Association, Wash. D.C. (1992) under the listings "Skin Conditioning agents," "emollients," "humectants," "miscellaneous" and "occlusive," each of these references is hereby incorporated by reference.

In preferred embodiments, emollients are chosen from the following nonlimiting list of general emollients, occlusive emollients and humectants. Examples of general emollients include short chain alkyl or aryl esters (C1–C6) of long chain straight or branched chain alkyl or alkenyl alcohols or acids (C8–C32) and their polyethoxylated derivatives; short chain alkyl or aryl esters (C1–C6) of C4–C12 diacids or diols optionally substituted in available positions by —OH; alkyl or aryl C1–C10 esters of glycerol, pentaerythritol, ethylene glycol, propylene glycol, as well as polyethoxylated derivatives of these and polyethylene glycol; C12–C22 alkyl esters or ethers of polypropylene glycol; C12–C22 alkyl esters or ethers of polypropylene glycol/polyethylene glycol copolymer; and polyether polysiloxane copolymers. In addition to many of the emulsifiers of preferred thickener systems, additional examples of occlusive emollients include cyclic and linear dimethicones, polydialkylsiloxanes, polyary/alkylsiloxanes, long chain (C8–C36) alkyl and alkenyl esters of long straight or branched chain alkyl or alkenyl alcohols or acids; long chain (C8–C36) alkyl and alkenyl amides of long straight or branched chain (C8–C36) alkyl or alkenyl amines or acids; hydrocarbons including straight and branched chain alkanes and alkenes such as squalene, squalane and mineral oil; jojoba oil polysiloxane polyalkylene copolymers, dialkoxy dimethyl polysiloxanes, short chain alkyl or aryl esters (C1–C6) of C12–C22 diacids or diols optionally substituted in available positions by OH such as diisopropyl dimer dilinoleate; and C12–C22 alkyl and alkenyl alcohols, long chain alkyl or aryl esters (C8–C36) of C12–C22 diacides or diols optionally substituted in available positions by —OH, such as diisostearyl dimer dilinoleate; lanolin and lanolin derivatives, and beeswax and its derivatives. Nonlimiting examples of preferred humectant type emollients include glycerol, propylene glycol, dipropylene glycol, polypropylene glycol, polyethylene glycol, sorbitol, pantothenol, gluconic acid salts and the like.

Although a thickener system is responsible for the stability and overall consistency of compositions of the present invention, emollients may also affect the viscosity, stability, and melt temperature of a composition. It is anticipated that a single emollient may be added to the present invention or two or more emollients may be added to the composition. A wide range of emollients may be added to the formulations of the present invention. Preferably wax and oil type emollients along with water soluble emollients are used. In a preferred embodiment, emollient systems are comprised of humectants in addition to occlusive wax and oil emollients in concentrations which achieve a moisturizing but not greasy composition which maintains and improves the condition of the skin upon repeated use. Ideally, emollients are non-comedogenic and are chosen to ensure no skin irritation or sensitization reaction occurs. This is particularly critical since the composition of the present invention will likely be worn in an occluded condition under surgical gloves. Furthermore, emollients should be chosen which do not affect the integrity of the glove material. For example, since hydrocarbon emollients such as mineral oil and petrolatum can detrimentally affect the tear strength of surgical gloves, these emollients should be avoided for compositions employed as presurgical disinfectants.

Without being bound or limited by theory, it is believed that if emollients are added to the present compositions, they may be present in four distinct regions. The emollients could occur (1) as a soluble species in the solvent phase, (2) dispersed as emulsified droplets within the mixed emulsifier micelle or crystalline gel network, (3) incorporated into the mixed emulsifier micelle or crystalline gel network, or (4) as a separate and distinct emulsion. As earlier stated, emollients can affect the melt temperature of a composition. Those emollients that are soluble or dispersible in the solvent phase tend to have little or no affect on the melt temperature and are therefore preferred. These emollients include the humectant and general emollients. The most preferred general emollients are those which are essentially insoluble in water but soluble in the hydroalcoholic solvent. These emollients are also preferred since they remain soluble and uniformly dispersed even above the melt temperature so that upon cooling to room temperature a uniform composition results.

In addition, they are also believed to have little effect on surgical gloves. Such general emollients typically do not have alkyl or alkenyl chains greater than about 14, preferably not greater than 12 and most preferably not greater than about 9 carbon atoms.

Those emollients which are insoluble in the hydroalcoholic solvent may associate with the emulsifiers of the thickener system and/or may incorporate into the micelle or crystalline gel network. Preferred emollients within this class are those emollients that are very hydrophobic since they tend to maintain a high melt temperature. For example, lanolin was found to increase the high temperature viscosity of certain thickener systems. Those emollients which are capable of associating with and disrupting the emulsifiers of the thickener system tend to decrease the melt temperature and may influence the stability of the composition. Certain branch alkyl esters of greater than about 12 carbon atoms per hydrophobe have been found to be particularly effective at decreasing the melt temperature. For example, trioctyldodecyl citrate has been found to significantly decrease the melt temperature of some systems.

Emollients which become incorporated into the thickener system tend to decrease the melt temperature. For example, laureth-4 (Brij 30) appears to incorporate into the thickener system since it does not phase out when heated above the melt temperature at concentrations below about 1% by weight. Laureth-4 also tends to decrease the melt temperature of the composition.

Certain emollients which are insoluble in the hydroalcoholic solvent can be emulsified in what is believed to be a separate and distinct emulsion. These emollients have little affect on the melt temperature of a composition. For example, certain cyclic silicones, polysiloxanes, and dialkoxypolysiloxanes can be emulsified in hydroalcoholic solvents using polyether/polysiloxane copolymer surfactants. Cyclic silicones such as DC344 (available from Dow Corning of Midland, Mich.) in the presence of certain polyether/polysiloxane copolymer surfactants such as Abil B88183 available from Goldschmidt Chemical Corp. of Hopewell, Ga. can form a thermally stable emulsion such that the compositions remain uniform both above and below the melt temperature. In fact, the combination of a long chain dialkoxypolysiloxane and polyether/polysiloxane copolymer has been found to actually promote the stability of certain thickener systems. The dialkoxypolysiloxane is believed to interact with the thickener system as well as the polyether/polysiloxane copolymer. These compounds have the following structures:

Dialkoxy Dimethicones $$R—O—Si(CH_3)_2—O[Si(CH_3)_2—O]_z—Si(CH_3)_2—OR$$

where
  R is a straight chain alkyl group of 14–50, preferably 16–24 carbon atoms, and
  z=5–300

Polyether/polysiloxane Copolymers $$(CH_3)_3—Si—O—[Si(CH_3)R_{11}—O]_x[Si(CH_3)R_8—O]_y—Si(CH_3)_3$$

where
  x+y=5–400, and preferably 15–200; and
  $R_8$ is a polyether substituted alkyl group with the structure:

$$—R_9—O(C_2H_4O)_p(C_3H_6O)_qR_{10}$$

where
  $R_9$ is an alkyl group of 1 to 6 carbon atoms;
  $R_{10}$ is hydrogen or an alky group of 1–22 carbon atoms;
  $R_{11}$ is an alkyl group of 1 to 22 carbon atoms or phenyl;
  p=2–300, and preferably 8–100; and
  q=0–100.

Note that branched chain polysiloxanes modified as shown in the two structures above are also possible.

The following are nonlimiting examples of emulsifier/emollient components which improve thickening/stability of compositions of the present invention.

a. Certain wax emulsifier/emollients have been found to be particularly useful and include solid waxy esters such as: Myristyl Myristate, Cetyl Palmitate, Myristyl Stearate, Stearyl Behenate, Behenyl Isostearate, Isostearyl Behenate, Behenyl Behenate, Lauryl Behenate, Behenyl Erucate. These have the following formula:

$$R_1—CO_2—R_2$$

where:
  $R_1$ is at least 14 carbon atoms; and
  $R_2$ is an alkyl or alkenyl of at least 4 carbon atoms.

b. Long chain hydrocarbon di-esters, tri-esters, of polyhydric alcohols with melting point greater than 23° C. include solid esters such as glycerol tribehenate and sorbitan tristearate.

c. Pure lanolins and lanolin derivatives (e.g. hydrogenated lanolin) provide excellent emolliency but can also improve the stability of the emulsion when used in combination with oil emollients.

e. Petrolatums provide excellent emolliency but can also improve the stability of the emulsion when used in combination with oil emollients. Petrolatums are mixtures of oily and waxy long chain hydrocarbons.

f. Microcrystalline waxes and branched hydrocarbon waxes with a melting point greater than 50° C. and a molecular weight greater than 400. An example of this includes but is not limited to Vybar 103 which is a branched hydrocarbon with a number average molecular weight of 2800 and is available from Petrolite Corp. of Tulsa, Okla. and "ULTRAFLEX" which is a microcrystalline wax also available from Petrolite Corp.

g. Oxidized waxes and modified hydrocarbon waxes may find application in the present invention. These are prepared from waxes modified by oxidation, salts of oxidized waxes, maleic anhydride adducts of polyolefins and urethane derivatives of oxidized synthetic or petroleum waxes. Applicable waxes could include Petrolite's "CARDIS" or "PETRONAUBA" microcrystalline and polyethylene-based oxidized products, "POLYMEKON" (salts) and "CERAMER" (anhydride adducts).

h. Fully saturated homopolymers of polyethylene or copolymers of various alkene monomers may be used to form polymers with a molecular weight at or below 3,000 with a melting point below 130° C. and low melt viscosities. Applicable waxes could include "POLYWAX" available from Petrolite Corp.

Fragrances

The formulations may also comprise a fragrance. If fragrances are included the fragrances must be chosen carefully since some fragrances are known to cause skin irritation and/or sensitization reactions.

Antimicrobials

In addition to the lower alcohols present in the composition of the present invention, other antimicrobials may be added to enhance the antimicrobial action of the compositions of the present invention. This may be particularly desirable in critical uses such as presurgical hand scrubs or presurgical patient skin scrub replacements. Suitable additional antimicrobials include iodine and its complexed forms such as povidone/iodine, chlorhexidine salts such as chlorhexidine digluconate (CHG), parachlorometaxylenol (PCMX), triclosan, hexachlorophene, Lauricidin; phenols, surfactants comprising a long chain hydrophobe (C12–C22) and a quaternary group, quaternary silanes, hydrogen peroxide, silver, silver salts such as silver chloride, silver oxide and silver sulfadiazine and the like. In order to reduce chances for irritation and yet maintain efficacy, the antimicrobial level should be adjusted to the minimum level which maintains a low bacteriological count for 6 and most preferably for 12 hours after application.

The most preferred additional antimicrobial is chlorhexidine since it is capable of ensuring long term antimicrobial efficacy. If chlorhexidine is added to the present invention it is preferably present as a soluble salt. The diacetate and digluconate salts are preferred. The most preferred antimicrobial is chlorhexidine digluconate (CHG). CHG is preferably present at a concentration of 0.05–5.0%, more preferably from 0.1–3% and most preferably from 0.25–2% by weight. Chlorhexidine is a bis(diguanide) and therefore is very basic and is capable of forming multiple ionic bonds with anionic materials. For this reason, in chlorhexidine-containing compositions, thickener systems are preferably based on non-ionic and/or cationic emulsifiers. Certain zwitterionic, very insoluble, or non-precipitating anionic emulsifiers may also be useful.

Foams

The compositions of the present invention may also be formulated into an aerosol foam or mousse by addition of an appropriate propellant. The propellant must be chosen to ensure proper delivery from the container to prevent clogging of the valve. The propellant can be chosen from chlorofluorocarbons (CFCs), hydrochlorofluorocarbons (HCFCs), hydrofluorocarbons (HFCs), perfluorinated alkanes, and lower alkanes (C1–C5) as well as nitrous oxide dimethyl ether and other solvent-soluble propellants. Preferred propellants are lower alkanes such as propane, butane, and isobutane since these result in a dramatic loss in viscosity making the formulation easy to dispense. A 70/30 mixture of propane/isobutane is a particularly preferred embodiment. In order to produce an aerosol composition the antimicrobial lotion is first formulated and charged into an appropriate pressure rated container. If convenient, the formulation may be heated above the melt temperature in order to facilitate filling. The propellant is then added under pressure at approximately 2–30% preferably 3–20% by volume. The propellant may form a separate layer or may remain emulsified in the composition.

Alternate Applications for Hydro-alcoholic Liquid Crystalline Solutions Incorporating Therapeutic or Active Ingredients The compositions of this invention may be compounded with UV absorbers and oils to deliver fast-drying sunscreens. Antimicrobials such as benzoyl peroxide may also be added to the formulations and the formulations may be useful as acne medication. The systems of the present invention may also be formulated with barrier compounds to form barrier creams and lotions. Materials which may be added to provide barrier protection for use as skin barriers to protect against diaper rash include but are not limited to 0.1 to 60% aldioxa, allantoin, aluminum acetate, aluminum hydroxide, bismuth subnitrate, boric acid, calamine, cellulose (microporous), cholecalciferol, cocoa butter, cod liver oil (in combination), colloidal oatmeal, cysteine hydrochloride, dexpanthenol, dimethicone, glycerin kaolin, lanolin (in combination), live yeast cell derivative, mineral oil, peruvian balsam, peruvian balsam oil, pertrolatum, protein hydrolysate (1-leucine, 1-isoleucine, 1-methionine, 1-phenylalanine, and 1-tyrosine), racemethionine, shark liver oil, sodium bicarbonate, sulfur, talc, tannic acid, topical starch, vitamin A, white petrolatum, zinc acetate, zinc carbonate and zinc oxide. Formulations are also contemplated containing antifungal agents for treating fungal infections of the skin such as athlete's foot and the like.

Since many of the compositions of the present invention contain antimicrobials, it is important that they be dispensed in an efficacious and precise amount. The compositions of the present invention can be dispensed in a discreet, substantially uniform amount using the dispensers disclosed in Applicants' Assignee's Copending U.S. patent application Ser. Nos. 08/668,198, filed Jun. 21, 1996, entitled "Dispenser for Antimicrobial Liquids" and No. 08/668,270, filed Jun. 21, 1996, entitled "Drip Resistant Nozzle for a Dispenser."

Methods of Preparation

The compositions of the present invention may be prepared by a variety of techniques. For example, the process can often be as simple as adding the thickener system to the hydroalcoholic solvent at a temperature above the melting point of the emulsifiers, mixing briefly and cooling. Nevertheless, to ensure a composition of maximum stability the components are preferably subjected to high shear (e.g. homogenized) for a limited time period while above the melting point of the thickener system followed by low shearixing while cooling. The system should be mixed under high shear long enough to ensure a very small "droplet" size, however, excessive high shear mixing may result in decreased viscosity and stability.

The cooling rate may be important depending on the particular thickener system. Certain thickener systems can be homogenized and then allowed to cool slowly, however, rapid cooling appears beneficial for most systems.

The order of adding the components may also affect the stability and viscosity of the system. In general it works well to melt the mixed emulsifiers with solvent-insoluble emollients together in one vessel. The hydroalcoholic solvent and any solvent miscible emollients are mixed in a second vessel. Both components are heated above the melting temperature of the thickener system. The hot liquid components are mixed together rapidly followed by approximately 1 to 5 minutes of homogenization for typical batches under 500 grams. While still low in viscosity the system is stirred using moderate agitation and cooled. It is also possible to add the molten thickener system along with any solvent insoluble emollients to hot water (i.e., water at a temperature above the melting temperature) followed by high shear mixing and subsequent dilution with alcohol. The processing variables including amount and intensity of high shear mixing, rate of cooling, and order of addition are easily determined by one skilled in the art.

Test Methods

Viscosity

In the following Examples (except where indicated) viscosity was measured at 23° C. at ambient pressure using a Brookfield LVDV-I+ viscometer equipped with a model D Brookfield heliopath and T spindles B–F. The spindle and speed was chosen for each particular sample such that the viscometer was operating in the middle of its range. All samples were allowed to equilibrate at 23° C. for 24 hours prior to measurement. Preferably the viscosity is taken at the lowest speed possible while staying within 20–80% of the viscometer range and more preferably between 30–70% of the range. In all cases the sample size and container geometry was chosen to ensure that there were no wall effects. By "wall effects" it is meant the viscosity value is not affected by the container and is essentially equivalent to the viscosity taken in an infinitely large container. For this reason lower viscosity samples required a larger sample size to accommodate the larger spindles. The following table outlines the preferred spindles for various sample viscosities.

| Sample Viscosity | T Spindle to Use |
|---|---|
| 1,000–100,000 | A or B |
| 10,000–200,000 | C |
| 50,000–500,000 | D |
| 100,000–1,250,000 | E |
| 500,000–3,000,000 | F |

The viscosity of each sample was taken as the highest relatively stable reading achieved on the first path the spindle traversed using the heliopath adapter.

Stability

The stability of samples was measured 24 hours after conditioning at ambient conditions by placing 12 ml of a formulation that formed a lotion/cream in a 15 ml graduated centrifuge tube. The tube was then centrifuged in a Labofuge B (Heraeus Sepatech GmbH, Model 2650, rotor 2150 and buckets #2101) at 3000 rpm (2275×g as measured at the longitudinal midpoint of the sample tube) for 30 minutes at 23° C. Stability is recorded as a volume percent separation in the Examples below.

Melt Temperature (Tm)

The melt temperature was measured by placing approximately 15 grams sample in a 25 cc sealed glass vial and placing the vial in a water bath. The temperature of the bath was increased periodically in discrete increments and the contents checked after approximately 1 hour at a given temperature. The melt temperature was taken as the temperature at which the mixture became very low in viscosity.

EXAMPLES AND COMPARATIVE EXAMPLES

The following Examples are provided to illustrate the invention but are not intended to limit the scope of the invention.

Example 1

This example demonstrates the utility of using longer linear alcohol ethoxylates in compositions of the present invention.

The following formulations were prepared by placing all ingredients in a jar and heating the solution to 65° C. for 30 minutes and then cooling to ambient temperature.

| | Formula | |
|---|---|---|
| | A | B |
| Component | Amount (grams) | |
| Unithox D-150, 25% Unithox 550 dispersion[1] | 7.50 | |
| Unithox D-100, 25% Unithox 450 dispersion[2] | | 7.50 |
| BE-22, Behenyl Alcohol | 0.67 | 0.67 |
| 190 Ethanol | 41.69 | 41.69 |
| Distilled Water | 10.81 | 10.81 |

-continued

| | Formula | |
|---|---|---|
| | A | B |
| Component | Amount (grams) | |
| Viscosity (cps)[3] Ambient | 85,630 | >300,000 |
| 40° C. | | 123,400 |
| 45° C. | | 147,800 |

[1]Manufactured by Petrolite Corp., Tulsa, OK; Unithox 550 has a carbon chain length of C38.
[2]Manufactured by Petrolite Corp., Tulsa, OK; Unithox 450 has a carbon chain length of C31.
[3]Measured using a TC spindle on a Helipath Viscometer rotating at 0.3 rpm.

The above formulations demonstrate the use of long chain alkyls C31 and C38 polyethoxylated alcohols.

Example 2

This Example demonstrate hat a three-component thickener system using one emulsifier having a hydrophobic-hydrophilic-hydrophobic structure (X-5175 and X-1069) is useful in preparing compositions of the present invention.

The following emulsions were made by heating both oil and water phases to 80° C. The oil phase consisted of BE-22, BB-5, Cetyl Palmitate, X-5175, Pripure 3786 and squalane. The water phase consisted of PEG 600, PEG 900, Glycerol, Dimethicone L45/350 NaCl and water. The two phases were then mixed together, homogenized, and then the composition was allowed to cool to ambient temperature. Once the composition was cooled, the ethanol was added and the mixture was lightly homogenized.

| Component | A Amount (grams) | B |
|---|---|---|
| BE-22[2] | 0.67 | 0.67 |
| BB-5[3] | 0.90 | 0.90 |
| Cetyl Palmitate[4] | 0.13 | 0.13 |
| X-5175[5] | 0.30 | |
| Pripure 3786, Diisopropyl Dimerate[6] | 0.90 | 0.90 |
| X-1069[7] | | 0.30 |
| Squalane | 0.90 | 0.90 |
| PEG 900[8] | 0.75 | 0.75 |
| PEG 600[9] | 0.32 | 0.32 |
| Glycerol | 0.43 | 0.43 |
| Dimethicane L45/350[10] | 0.30 | 0.30 |
| NaCl | 0.04 | 0.04 |
| Distilled Water | 15.47 | 15.47 |
| 190 Ethanol | 38.95 | 38.95 |
| Viscosity (cps)[1] | | |
| Ambient, 0.3 rpm | 111,900 | 94,060 |
| 40° C., 1.5 rpm | 18,940 | — |
| 40° C., 12 rpm | — | 1,650 |
| 45° C., 12.0 rpm | 1,875 | — |

[1]All viscosities were measured using a TC spindle on a Helipath viscometer
[2]Behenyl Alcohol manufactured by M. Michel Co. Inc., New York, NY
[3]Beheneth-5 manufactured by Nikko Chemicals Co., LTD, Tokyo, Japan
[4]Available from Henkel Corp., Hoboken, NJ
[5]Acetate ester of Unithox 480, approximately C32-(polyethyleneoxide)$_{40}$-Acetate; manufactured by Petrolite Corp., Tulsa, OK
[6]Diisopropyl Dimerate available from Unichema North America, Chicago, IL.
[7]Unithox 420 capped with 75% propylene oxide, approximately (C31-(PEO)$_3$(PPO)$_{29}$, manufactured by Petrolite Corp.
[8]Polyethylene glycol, molecular weight = 900
[9]Polyethylene glycol, molecular weight = 600
[10]Polydimethysiloxane, Union Carbide Corp., Danbury, CT.

Example 3

This Example demonstrates that a two-component thickener system using one emulsifier having a hydrophobic-hydrophilic-hydrophobic structure (X5171) is useful in preparing compositions of the present invention.

The viscosity was taken at ambient temperature using a TA spindle on a Helipath Viscometer at 0.3 rpm unless otherwise noted. Fifteen milliliters of each formulation was centrifuged in an American Scientific Products Labofuge B centrifuge at 3,000 rpm for 30 minutes to determine the stability measured as the percent separation by volume of each formulation.

| | Component (grams) | | | | | | | | | |
|---|---|---|---|---|---|---|---|---|---|---|
| Sample | Emerest™[4] 2350 | Emerest™[5] 2380 | Unithox™[6] 420 | Unithox™[7] 450 | Unithox™[8] 480 | Unilin™[9] 425 | 190 Ethanol | Distilled Water | Viscosity (cps) | % separation by Volume |
| A | 2.00 | 2.00 | 2.00 | — | — | 1.00 | 75.8 | 68.2 | 50,380 | .95 |
| B | 2.00 | 2.00 | — | 2.00 | — | 1.00 | 75.8 | 68.2 | 41,750 | 0 |
| C | 2.00 | 2.00 | — | — | 2.00 | 1.00 | 75.8 | 68.2 | 38,690 | 0 |
| D | 2.00 | 2.00 | 2.00 | — | — | 1.00 | 106.1 | 37.9 | 103.5[1] | 19 |
| E | 2.00 | 2.00 | — | 2.00 | — | 1.00 | 106.1 | 37.9 | 14,310 | .95 |
| F | 2.00 | 2.00 | — | — | 2.00 | 1.00 | 106.1 | 37.9 | 1,905[2] | .95 |
| G | 2.00 | 2.00 | 2.00 | — | — | 1.00 | 136.4 | 7.6 | 45.8[3] | 57 |
| H | 2.00 | 2.00 | — | 2.00 | — | 1.00 | 136.4 | 7.6 | 56.4[3] | 48.6 |
| I | 2.00 | 2.00 | — | — | 2.00 | 1.00 | 136.4 | 7.6 | 25.5[3] | 0 |

[1]50 rpm
[2]2.5 rpm
[3]100 rpm
[4]Ethylene glycol monostearate available from Henkel Corp.
[5]Propylene glycol monostearate available from Henkel Corp.
[6]Unithox 420 C31-3EO available from Petrolite Corp.
[7]Unithox 450 C31-10EO available from Petrolite Corp.
[8]Unithox 480 C31-40EO available from Henkel Corp.
[9]Unilin 425 available from Henkel Corp.

The following formulation was prepared by heating the solution to 65° C. until dissolved, and then allowing the formulation to cool to ambient temperature.

| Component | Amount (grams) |
|---|---|
| BE-22 | 0.67 |
| X-5171[1] | 0.90 |
| Distilled Water | 15.47 |
| 190 Ethanol | 38.95 |
| Viscosity (cps)[2] | 4,281 |

[1]Lauric ester of Unithox 480; approximately C31-(polyethylene oxide)$_{40}$-Laurate; manufactured by Petrolite Corp., Tulsa, OK.
[2]Measured at ambient temperature using a TC spindle on a Helipath Viscometer at 6 rpm.

Example 4

This Example demonstrates that polyhydric alcohol esters, ethyoxylated fatty alcohol and fatty alcohols together form thickener systems useful in preparing compositions of the present invention. This Example also demonstrates the importance of HLB and alcohol level in forming a viscous stable emulsion.

The following formulations were prepared by placing the Emerest® stearates (polyhydric alcohol esters) available from Henkel Corp. of Hoboken, N.J., the Unithox® ethoxylates (polyethyoxylated fatty alcohols) available from Petrolite Corp. and the Unilin® alcohol (alkyl alcohol) available from Petrolite Corp. in a glass vial and heating the mixture to 115° C. until molten and swirling to mix. This was then added to the alcohol water mixture which had been heated to 70° C. The solution was then homogenized for 30 seconds at high speed, then immersed in cool water and homogenized at the lowest speed for 1 minute. The formulation was then allowed to cool and equilibrate to ambient temperature overnight before the viscosity and stability testing.

As the amount of ethanol increased, the stability and viscosity of the samples decreased.

Example 5

This example demonstrates that single emulsifier thickening systems based on fatty alcohol ethoxylates are useful in preparing compositions of the present invention.

The following solutions were prepared by placing the contents in a 4-oz. jar and heating the contents to 65° C. until the contents dissolved. The clear, hot solutions were then removed from the heat and allowed to cool to ambient temperature.

Separation of each sample was tested as described in Example 3.

| | Formula | | |
|---|---|---|---|
| | A | B | |
| Component | Amount (grams) | | C |
| Beheneth-5[1] | — | — | 0.96 |
| BRIJ 72[2] | 1.8 | 1.8 | — |
| 190 Proof Ethanol | 38.0 | 41.7 | 42.26 |
| Deionized Water | 20.2 | 16.5 | 16.78 |

-continued

| | Formula | | |
|---|---|---|---|
| Component | A | B | C |
| | Amount (grams) | | |
| Viscosity (cps) | 63,310[3] | Not Stable | 4,703[4] |
| Separation (by volume) | 0 | Not stable | 0 |

[1]Available from Nikko Chemicals Co., LTD, Tokyo, Japan (beheneth-5)
[2]Polyethoxylated fatty alcohol steareth-2 available from ICI Surfactants of Wilmington, DE
[3]Viscosity was measured using a TC spindle on a Helipath Brookfield Viscometer at 0.6 rpm at ambient temperature.
[4]Viscosity was measured using a TC spindle on a Helipath Brookfield Viscometer at 6 rpm at ambient temperature In Formula B having an increased alcohol level, the 18 carbon chain did not form a stable system; however, in Formula C, with an even higher ethanol level, the 22 carbon chain creates a stable system.

Example 6

This example illustrates that an additional antimicrobial such as chlorohexidine gluconate can be added to formulations of the present invention.

The following formulations were prepared by heating the solutions in clean 4-oz. jars in an oven to 65° C. The formulations did not contain the CHG at this point. Once the solutions had cooled to ambient temperature and were allowed to thicken, the aqueous CHG solution was added and mixed.

| | Sample | | | | |
|---|---|---|---|---|---|
| Component | A | B | C Amount (grams) | D | E |
| Beheneth-5 | 0.90 | 0.90 | 0.90 | 0.90 | 0.90 |
| Behenyl Alcohol | 0.36 | 0.36 | 0.36 | 0.36 | 0.36 |
| 190 Proof Ethanol | 42.05 | 41.83 | 41.62 | 41.19 | 40.33 |
| Distilled Water | 16.69 | 15.35 | 14.0 | 11.31 | 5.93 |
| CHG (0.2048 g/ml) | — | 1.56 | 3.12 | 6.24 | 12.48 |

The samples were tested to determine the level of CHG inactivation and were compared to the commercially available hand preparation Hibiclens™, available from Stuart Pharmaceuticals of Wilmington, Del. Bacterial spore suspension trypticase soy agar plates were made by adding 0.5 ml of *Bacillus subtilus* ATCC 6633 at a density of $1\times10^8$ spores/ml to molten (50° C.) agar. Twenty (20) ml agar was dispensed into sterile petri dishes and the agar was allowed to solidify. Using a 4 mm diameter gel punch attached to a vacuum source, wells were formed in the agar plates. Using a micropipette, one sample was added to fill each well. The inoculated plates were incubated overnight at 35° C. The zone of inhibition for each well was measured. Zone size versus standard concentration was plotted on semi-log graph paper and the concentration of chlorohexidine in the sample was calculated from the standard curve.

The samples were also tested for stability by the method outlined in Example 3. The viscosity of the samples was taken using a Brookfield LVDV-I⁺ viscometer with a heliopath adapter at 23° C. with the rpm as listed in the table below

| Sample | Formulation CHG Conc. | % CHG released in Assay. | % CHG Inactivation | % Separation (by Volume) | Viscosity (cps) TC Spindle | RPM |
|---|---|---|---|---|---|---|
| A | 0 | No Activity | Not Applicable | 0 | 68,310 | .6 |
| B | 0.5 | 0.313 | 37 | 0 | 39,690 | .6 |
| C | 1.0 | 0.97 | 3 | 0 | 20,380 | 1.5 |
| D | 4.0 | 2.88 | 28 | 0 | 23,100 | 1.0 |
| HIBICLENS ™ | 4.0 | 2.87 | 28 | | —* | —* |

*Not determined

The above data shows that the solutions were compatible with CHG and the level of inactivation was consistent with what is typically seen in CHG-containing products.

Example 7

This example demonstrates the effect of combining a linear, primary alcohol of varying chain length (C16, C18, C20, C22 and ~C24) with an ethoxylated behenyl ether with 5 moles of ethylene oxide in compositions of the present invention.

Each formulation was prepared by placing all the components in the amounts designated in the table below into a jar. The jar was then heated to 65° C. for one hour until all components were dissolved. Due to the high melting point, the formulation containing C24 primary alcohol was homogenized at 65° C. The jar was then placed on a roller at 60 rpm and allowed to roll and cool for 24 hours. Viscosity was measured using a Helipath TC Spindle at the rpm shown in the table below at ambient temperature. Stability was measured as described in Example 4.

|  | Sample | | | | | | | |
|---|---|---|---|---|---|---|---|---|
|  | A | B | C | D | E | F | G | H |
| Component | Amount (grams) | | | | | | | |
| BB-5[1] | 0.96 | 0.96 | 0.96 | 0.96 | 0.96 | 0.96 | 0.96 | 0.96 |
| LANETTE 16[2] | — | 0.36 | — | — | — | — | — | — |
| LANETTE WAX O[3] | — | — | 0.36 | — | — | — | — | — |
| LANETTE 18[4] | — | — | — | 0.36 | 0.18 | — | — | — |
| AR-20[5] | — | — | — | — | 0.18 | 0.36 | — | — |
| BE-22[6] | — | — | — | — | — | — | 0.36 | — |
| UNILIN 350[7] | — | — | — | — | — | — | — | 0.36 |
| 190 Proof ETHANOL | 42.26 | 42.0 | 42.0 | 42.0 | 42.0 | 42.0 | 42.0 | 42.0 |
| Deionized WATER | 16.78 | 16.68 | 16.68 | 16.68 | 16.68 | 16.68 | 16.68 | 16.7 |
| Viscosity (cps) Heliopath, TC Spindle | 4,703 | 13,970 | 22,880 | 28,380 | 17,650 | 122,500 | 57,050 | 73,780 |
| rpm | 6.0 | 3.0 | 1.5 | 1.5 | 1.5 | 0.3 | 0.6 | 0.3 |
| % Separation (by Volume) | 0 | 0 | 0 | 0 | 0 | 0 | 0 | 0 |

[1]Beheneth-5, (C2 with 5 moles ethyloxide) available from Nikko Chemicals Co., LTD, Tokyo, Japan
[2]Cetyl alcohol (C16), available from Henkel Corp., Hoboken, NJ
[3]Cetearyl alcohol (Blend of C16/C18), available from Henkel Corp., Hoboken, NJ
[4]Stearyl alcohol (C18), available from Henkel Corp., Hoboken, NJ
[5]Aracadyl alcohol (C20), available from M. Michel Co. Inc., NY, NY
[6]Behenyl alcohol (C22), available from M. Michel Co. Inc., NY, NY
[7]Available from Petrolite Corp., Tulsa, OK.

Sample A containing a single polyethoxylated alcohol emulsifier produced a stable composition. Long chain fatty alcohols of C16 (Cetyl alcohol) and longer produced samples with more desirable viscosities (Samples B, C, D, E, F, G and H).

Example 8

This example demonstrates the effect of combining a linear, primary alcohol of varying chain length (C16, C18, C20, C22 and ≈C24) with polyethoxylated behenyl, either beheneth-10 or beheneth-20.

Each sample was prepared by placing all components in a 4-oz. jar. The jar was then heated in an oven to 65° C. until the components were molten or dissolved. The jar was then placed on a roller and the jar was rolled at 60 rpm for 24 hours while the sample cooled.

The viscosity of each sample was measured using a Helipath TC spindle at the rpm shown in the table below at ambient temperature on a Brookfield viscometer. Separation was tested as outlined in Example 3 above.

|  | A | B | C | D | E | F | G | H |
|---|---|---|---|---|---|---|---|---|
| Component | Amount (grams) | | | | | | | |
| BB-10[1] | 0.96 | 0.96 | 0.96 | 0.96 | 0.96 | — | — | — |
| BB-20[2] | — | — | — | — | — | 0.96 | 0.96 | 0.96 |
| LANETTE 16[3] | 0.36 | — | — | — | — | — | — | — |
| LANETTE 18[4] | — | 0.36 | — | — | — | 0.36 | — | — |
| AR-20[5] | — | — | 0.36 | — | — | — | 0.36 | — |
| BE-22[6] | — | — | — | 0.36 | — | — | — | 0.36 |
| UNILIN 350 | — | — | — | — | 0.36 | — | — | — |
| 190 Proof Ethanol | 42.0 | 42.0 | 42.0 | 42.0 | 42.0 | 42.0 | 42.0 | 42.0 |
| Deionized Water | 16.68 | 16.68 | 16.68 | 16.68 | 16.7 | 16.7 | 16.7 | 16.7 |
| Viscosity (cps) | Clear solution NA | 5,130[7] | 9,363[7] | 8,344[7] | 3,150[8] | Separated | Separated | Separated |

-continued

| Component | A | B | C | D | E | F | G | H |
|---|---|---|---|---|---|---|---|---|
| | | | | Amount (grams) | | | | |
| rpm | | 6.0 | 3.0 | 3.0 | * | | | |
| % Separation (by volume) | Clear Solution NA | 0 | 0 | 0 | 0 | NA | NA | NA |

[1]Beheneth-10 available from Nikko Chemicals Co., LTD., Tokyo, Japan
[2]Beheneth-20 available from Nikko Chemicals Co., LTD., Tokyo, Japan
[3]Cetyl Alcohol, available from Henkel Corp., Hoboken, NJ
[4]Stearyl alcohol, available from Henkel Corp., Hoboken, NJ
[5]Aracadyl alcohol, available from M. Michel Co. Inc., NY, NY
[6]Behenyl alcohol, available from M. Michel Co. Inc., NY, NY
[7]Helipath TC Spindle
[8]Helipath TA Spindle The above data demonstrates that the carbon chain length of the fatty alcohol and the amount of ethoxylation of the fatty alcohol is important in achieving a stable viscous emulsion. For example, formulations B, C & D produced stable viscous samples whereas formulations F, G and H which included an emulsifier with a longer polyethylene oxide chain produced unstable compositions.

Example 7, Samples A–H use beheneth-5, whereas Example 8, Samples A–E use beheneth-10 and Samples F–H use beheneth-20. At the highest level of ethyoxylation, the samples were not stable (F–H). Best results were achieved with the lowest level of ethyoxylation (Samples A–H, Example 7) and C20–C24 alcohols (Samples F–H).

Example 9

This example demonstrates. the effect of wax and oil emollients on the viscosity of compositions of the present invention. Formula A was prepared by placing all components in a glass jar and heating to 65° C. until all components were dissolved. The jar was placed on the bench and allowed to cool to ambient temperature. Formula A was then used to prepare formulae B through H. In each jar was placed 58 grams of A along with the specific emollients. The formulae were heated to 65° C., and were lightly homogenized and cooled to ambient temperature.

Each sample was tested for viscosity and stability as outlined in Example 4.

| | Sample | | | | | | | |
|---|---|---|---|---|---|---|---|---|
| Component | A | B | C | D | E | F | G | H |
| | | | | Amount (grams) | | | | |
| BB-5 | 40.5 | 0.87 | 0.87 | 0.87 | 0.87 | 0.87 | 0.87 | 0.87 |
| BE-22 | 16.2 | 0.35 | 0.35 | 0.35 | 0.35 | 0.35 | 0.35 | 0.35 |
| Myristyl Myristate | — | 0.50 | — | — | — | 0.50 | — | — |
| Behenyl Isostearate | — | — | 0.50 | — | — | — | 0.50 | — |
| Lanolin Emery HP-2060 | — | — | — | 0.50 | — | — | — | 0.50 |
| Isocetyl Alcohol | — | — | — | — | 1.50 | 1.50 | 1.50 | 1.50 |
| 190 Proof Ethanol | 1892.0 | 40.64 | 40.64 | 40.64 | 40.64 | 40.64 | 40.64 | 40.64 |
| Deionized Water | 751.3 | 16.14 | 16.14 | 16.14 | 16.14 | 16.14 | 16.14 | 16.14 |
| Viscosity (cps) TC Spindle | 70,000 | 134,100 | 165,000 | 158,400 | 12,310 | 400 | 60,000 | 124,700 |
| Stability (% by Volume) | 0 | 0 | 0 | 0 | 44.8 | 64.8 | 0 | 0 |

The viscosity and stability results of Samples E and F demonstrate that relatively short chain branched alcohols (e.g., Jarcol I-16™ C16 isocetyl alcohol available from Jarchem Industries Inc., Newark, N.J.) can reduce the viscosity and stability of the resultant emulsion. The inclusion of long chain, hydrophobic constituents such as Behenyl Isostearate and Lanolin (Samples G & H) significantly improves the tolerance of the emulsion for branched short chain oils such as isocetyl alcohol.

Example 10

This example demonstrates that monovalent salts of alkyl carboxylic acids of 16 carbon atoms and greater are useful as co-emulsifiers in the present invention.

The samples were prepared according to the formulae outlined in the table below by placing all components in a 4-oz. jar. The jar was capped and heated to 65° C. until all components were dissolved. The jar was then swirled to mix the components, removed from the heat and allowed to cool to ambient temperature. Viscosity measurements were taken as identified in the table. Separation tests were done as outlined in Example 3.

| | Sample | |
|---|---|---|
| | A | B |
| Component | Amount (grams) | |
| BB-5 | 0.96 | 0.96 |
| Sodium Stearate | 0.36 | 0.96 |
| 190 Ethanol | 42.00 | 41.60 |
| Deionized Water | 16.70 | 16.50 |
| Viscosity (cps) | 5,904[1] | 320,000[2] |
| % Separation (by Volume) | 0 | 0 |

[1]Measurements taken at ambient temperature using a TC Helipath Spindle at 0.3 rpm.
[2]Measurements taken at ambient temperature using a TD Helipath Spindle at 0.3 rpm.

Example 11

This example demonstrates the use of a behenyl ester with a polyhydric alcohol and glycerol monobehenate.

The sample was prepared by melting the glycerol mono Behenate, Beheneth-5, Unithox 480 and Diisopropyl Dimerate (oil phase) together. The oil phase and the water phase were separately heated to 180° F. The water phase consisted of PEG 900, PEG 600, Glycerol, Dimethicone L45/350, NaCl and distilled water. The oil phase and the water phase were then mixed by homogenization and cooled to ambient temperature. The Ethanol was then added to the combination and the resulting combination was homogenized on low speed for one minute.

| Component | Amount (grams) |
|---|---|
| Glycerol mono Behenate | 0.80 |
| Beheneth-5 | 0.90 |
| Unithox 480[1] | 0.21 |
| Diisopropyl Dimerate | 1.80 |
| PEG 900[2] | 0.75 |
| PEG 600[3] | 0.32 |
| Glycerol | 0.43 |
| Dimethicone L45/350 | 0.30 |
| NaCl | 0.07 |
| Distilled Water | 15.47 |
| 190 Proof Ethanol | 38.95 |
| Viscosity (cps) | 21,690 |

[1]Unithox ™ is a linear alcohol (80–85% primary), which has been ethoxylated. The number average molecular weight is 2,250 and ethylene oxide content is 80%. Available from Petrolite Corp., Tulsa, OK.
[2]Polyethylene glycol 900, available from Union Carbide, Danbury, CT.
[3]Polyethylene glycol 600 available from Union Carbide, Danbury, CT.

Example 12

This example demonstrates the sensitivity of the high temperature stability to the choice of oil emollient and coemulsifier concentration.

These samples were prepared according to the formulae outlined in the table below. The ethyl alcohol of the composition was not heated during manufacture. The oil/wax phase which consisted of behenyl alcohol, beheneth-5, Unithox 480, Isofol 18T18 ester, Pelemol ISB, Glycerol Triisotearate, Isofol 24, Isostearate and Isofol 1616 was heated separately from the water phase which consisted of PEG 600, PEG 900, Glycerol, Dimethicone L45/350 and NaCl. Both oil/wax and water phases were heated to 80° C. Once all components were dissolved, the oil phase was added to the water phase and the combination was homogenized and allowed to cool before adding the ethyl alcohol. The entire composition was then lightly homogenized.

| | Sample | | | | | | | | | | | | | |
|---|---|---|---|---|---|---|---|---|---|---|---|---|---|---|
| | A | B | C | D | E | F | G | H | I | J | K | L | M | N |
| Component | Amount (grams) | | | | | | | | | | | | | |
| Behenyl Alcohol | 0.78 | 0.78 | 0.80 | 0.80 | 0.78 | 0.78 | 0.80 | 0.80 | 0.78 | 0.80 | 0.78 | 0.80 | 0.78 | 0.80 |
| Beheneth-5 | 1.08 | 1.08 | 0.90 | 0.90 | 1.08 | 1.08 | 0.90 | 0.90 | 1.08 | 0.90 | 1.08 | 0.90 | 1.08 | 0.90 |
| Unithox ™ 480[1] | 0.05 | 0.05 | 0.21 | 0.21 | 0.05 | 0.05 | 0.21 | 0.21 | 0.05 | 0.21 | 0.05 | 0.21 | 0.05 | 0.21 |
| Isofol 18T18 ester[2] | 1.80 | 1.80 | 1.80 | 1.80 | 1.80 | 1.80 | 1.80 | 1.80 | — | — | — | — | 1.80 | — |
| Pelemol ISB[3] | 0.15 | — | 0.15 | — | 0.15 | — | 0.15 | — | — | — | — | — | — | — |
| Glycerol Triisostearate[4] | — | — | — | — | — | — | — | — | 1.80 | 1.80 | — | — | — | — |
| Isofol 24 Isostearate[5] | — | — | — | — | — | — | — | — | — | — | 1.80 | 1.80 | — | — |
| Isofol 1616[6] | — | — | — | — | — | — | — | — | — | — | — | — | — | 1.80 |
| PEG 900[7] | 0.75 | 0.75 | 0.75 | 0.75 | 2.10 | 2.10 | 0.75 | 0.75 | 0.75 | 0.75 | 0.75 | 0.75 | 0.75 | 0.75 |
| PEG 600[8] | 0.32 | 0.32 | 0.32 | 0.32 | 0.90 | 0.90 | 0.32 | 0.32 | 0.32 | 0.32 | 0.32 | 0.32 | 0.32 | 0.32 |
| Glycerol | 0.43 | 0.43 | 0.43 | 0.43 | 1.20 | 1.20 | 0.43 | 0.43 | 0.43 | 0.43 | 0.43 | 0.43 | 0.43 | 0.43 |
| Dimethicone L45/350[9] | 0.3 | 0.30 | 0.30 | 0.30 | 0.30 | 0.30 | 0.30 | 0.30 | 0.30 | 0.30 | 0.30 | 0.30 | 0.30 | 0.30 |
| NaCl | 0.07 | 0.07 | 0.07 | 0.07 | 0.07 | 0.07 | 0.07 | 0.07 | 0.07 | 0.07 | 0.07 | 0.07 | 0.07 | 0.07 |

-continued

| Component | A | B | C | D | E | F | G | H | I | J | K | L | M | N |
|---|---|---|---|---|---|---|---|---|---|---|---|---|---|---|
| | | | | | | | Sample Amount (grams) | | | | | | | |
| Distilled Water | 15.42 | 15.47 | 15.42 | 15.47 | 15.42 | 15.47 | 15.42 | 15.42 | 15.47 | 15.47 | 15.47 | 15.47 | 15.47 | 15.47 |
| Ethanol (190 Proof) | 38.85 | 38.95 | 38.95 | 38.95 | 38.95 | 38.95 | 38.95 | 38.95 | 38.95 | 38.95 | 38.95 | 38.95 | 38.95 | 38.95 |

[1]Unithox ™ 480 is a linear alcohol, 80–85% primary, which was ethoxylated and has an Mn of 2,250; ethylene oxide content is 80%. Manufactured by Petrolite Corp. of Tulsa, OK.
[2]Available from Vista Chemical, Houston, TX.
[3]Available from Phoenix Chemical, Somerville, NJ
[4]Available from Unichema International, Chicago, IL
[5]Available from Vista Chemical, Houston, TX.
[6]Available from Vista Chemical, Houston, TX.
[7]Polyethylene glycol, molecular weight = 900; Available from Dow Chemical Co., Midland, MI.
[8]Polyethylene glycol, molecular weight = 600 (Carbowax ™ 600); Available from Union Carbide, Houston, TX
[9]Dimethicone from Union Carbide with a viscosity of 350 centistokes.

A Brookfield Helipath Viscometer with a TC spindle was used to check viscosity of each sample at the temperature and at the rotation listed in the table below. No phase separation of the samples was observed even after heating to 40° C. or to 47° C.

Viscosity at Given Temperature

| Sample | Ambient | | 30° C. | | 40° C. | | 47° C. | |
|---|---|---|---|---|---|---|---|---|
| | rpm | cps | rpm | cps | rpm | cps | rpm | cps |
| A | 0.3 | 100,600 | 1.5 | 14,500 | 3 | 9,031 | 30 | 668 |
| B | 0.6 | 46,000 | 3 | 8,188 | 6 | 4,469 | 60 | 337 |
| C | 0.3 | 161,900 | 1.5 | 18,630 | 3 | 8,844 | 30 | 1,025 |
| D | 0.3 | 118,800 | 1.5 | 15,060 | 3 | 7,831 | 12 | 2,023 |
| E | 0.3 | 103,100 | 1.5 | 16,940 | 3 | 10,410 | 12 | 2,117 |
| F | 0.3 | 93,440 | 1.5 | 17,500 | 3 | 9,500 | 30 | 671 |
| G | 0.3 | 172,200 | 1.5 | 22,000 | 3 | 10,660 | 12 | 2,922 |
| H | 0.3 | 130,300 | 1.5 | 15,960 | 3 | 8,688 | 12 | 2,133 |
| I | 0.3 | 88,750 | 1.5 | 18,880 | 3 | 10.250 | 12 | 2,086 |
| J | 0.3 | 236,900 | 0.6 | 52,970 | 1.5 | 22,810 | 3 | 12,340 |
| K | 0.3 | 82,810 | 1.5 | 15,250 | 1.5 | 15,060 | 30 | 1,019 |
| L | 0.3 | 198,400 | 1.5 | 21,630 | 1.5 | 15,060 | 1.5 | 16,500 |
| M | 0.6 | 41,560 | 3 | 8,561 | 3 | 7,025 | 60 | 362 |
| N | 0.3 | 171,600 | 1.5 | 19,190 | 1.5 | 14,440 | 6 | 4,750 |

Example 13

This example demonstrates coemulsifing waxes increase the viscosity of the resultant composition at ambient and at elevated temperatures. Samples were prepared by melting the oil/wax/polyethoxylate apart from the water. Both oil and water phases were heated to 80° C., mixed by homogenizer, cooled and then the ethyl alcohol was added.

| Component | A | B | C | D | E | F | G | H | I | J |
|---|---|---|---|---|---|---|---|---|---|---|
| | | | | | SAMPLE Amount (grams) | | | | | |
| Behenyl Alcohol | — | 0.70 | — | — | 0.70 | — | 0.70 | — | 0.70 | 0.70 |
| Aracadyl Alcohol | 0.70 | — | 0.70 | 0.70 | — | 0.70 | — | 0.70 | — | — |
| Beheneth-5 | 1.10 | 1.10 | 1.10 | 1.10 | 1.10 | 1.10 | 1.10 | 1.10 | 1.10 | 1.10 |
| Isofol 2414 | 1.80 | 1.80 | 1.80 | 1.80 | 1.80 | 1.80 | 1.80 | 1.80 | 1.80 | 1.80 |
| Vybar 103[1] | — | — | .50 | — | — | — | — | — | — | — |
| Tetraglycerol pentastearate | — | — | — | .50 | 0.50 | — | — | — | — | — |
| Glycoltribehenate | — | — | — | — | — | .50 | 0.50 | — | — | — |
| Sorbitan tristearate | — | — | — | — | — | — | — | .50 | 0.50 | — |
| Sorbeth-6 Hexastearate | — | — | — | — | — | — | — | — | — | 0.50 |
| Distilled Water | 13.34 | 13.34 | 13.20 | 13.20 | 13.20 | 13.20 | 13.20 | 13.20 | 13.20 | 13.20 |

-continued

| Component | \multicolumn{10}{c}{SAMPLE} |
|---|---|---|---|---|---|---|---|---|---|---|
| | A | B | C | D | E | F | G | H | I | J |
| | \multicolumn{10}{c}{Amount (grams)} |
| CHG[2] | 3.12 | 3.12 | 3.12 | 3.12 | 3.12 | 3.12 | 3.12 | 3.12 | 3.12 | 3.12 |
| 190 Proof Ethanol | 39.94 | 39.94 | 39.58 | 39.58 | 39.58 | 39.58 | 39.58 | 39.58 | 39.58 | 39.58 |

[1]Branched hydrocarbon; number average molecular weight of 2800; available from Petrolite Corp., Tulsa, OK.
[2]20.48 g/ml in water available from Xttrium Labs of Chicago, Illinois.

Each of the samples was tested for viscosity using a TC Helipath spindle at 0.3 rpm at ambient temperature and at 30° C. The results are outlined in the table below.

| Sample | Viscosity (cps) at 23° C. | Spindle rpm | 30° C. viscosity (cps) |
|---|---|---|---|
| A | 141,900 | 1.5 | 15,940 |
| B | 76,250 | 3 | 6,250 |
| C | 229,100 | 0.6 | 39,690 |
| D | 113,800 | 0.3 | 101,600 |
| E | >300,000 | 0.3 | 127,500 |
| F | 65,730 | 0.6 | 47,190 |
| G | 115,000 | 0.6 | 37,500 |
| H | 127,800 | 0.3 | 121,900 |
| I | >300,000 | 0.3 | 100,000 |
| J | 516,300 | 0.3 | 188,800 |

Example 14

This example demonstrates a silicone co-emulsifier is useful in the present invention. The emulsifier is a triblock copolymer of dimethicone, polyethylene oxide and a behenate ester.

The oil phase consisted of behenyl alcohol, beheneth-5, Isofol 2414 and dimethicone copolyol phosphobehenate. The water phase consisted of distilled water and CHG. The water and oil phases were heated separately to 80° C. to allow the components to melt and each was swirled to mix. The two phases were combined and homogenized 30 seconds on high speed. The combination was allowed to cool.

Once the mixture was cool and ethanol was added, the combined mixture was homogenized. After the sample was prepared, the viscosity was tested at ambient temperature and at 30° C. using a TC Helipath Spindle at 0.3 rpm. Results are shown in the table below.

| Component | Amount (grams) | |
|---|---|---|
| Behenyl Alcohol | | 0.70 |
| Beheneth-5 | | 1.10 |
| Isofol 2414 | | 1.80 |
| Dimethicone Copolyol Phosphobehenate | | 0.50 |
| Distilled Water | | 13.20 |
| CHG[1] | | 3.12 |
| 190 Proof Ethanol | | 39.58 |
| Viscosity (cps) | Temperature Ambient | 223,800 |
| | 30° C. | 76,560 |

[1]0.2048 g/ml in water available from Xttrium Labs of Chicago, Illinois

Example 15

The following includes a preferred formulation of the invention.

The oil phase consisted of behenyl alcohol, cetyl palirtate, beheneth-5, Unithox 480, diisopropyl dimerate and squalane. The oil phase components were combined and were heated at 80° C. until all components were melted. The oil phase was then swirled to mix the solution. The aqueous phase consisted of PEG 900, PEG 600, glycerol, dimethicone L45/350, NaCl and distilled water. The aqueous phase components were combined and heated to 80° C. The oil phase was then added to the aqueous phase and the resultant combination was homogenized on high speed for 30 seconds. The homogenized composition was cooled to ambient temperature. Once the composition was cool, ethanol was added and the resultant combination was lightly homogenized.

| Component | Amount (grams) |
|---|---|
| Behenyl alcohol | 7.77 |
| Cetyl Palmitate | 1.54 |
| Beheneth-5 | 10.50 |
| Unithox 480 | 2.45 |
| Diisopropyl Dimerate | 10.50 |
| Squalane | 10.50 |
| PEG 900 | 8.75 |
| PEG 600 | 3.71 |
| Glycerol | 5.04 |
| Dimethicone L45/350 | 3.50 |
| NaCl | 0.42 |
| Distilled Water | 180.56 |
| Ethanol (190 Proof) | 454.76 |

The formulation was first evaluated in tactile testing by applying 2 ml in the palm of one hand and rubbing the lotion thoroughly into both hands. This composition had good cosmetic properties. A panel of five volunteers then applied the lotion as described eight times a day in approximately 1 hour intervals after first washing with water and Ivory liquid soap (Procter and Gamble, Cincinnati, Ohio) and drying the hands thoroughly before each application. This was repeated for a total of 5 days and was conducted during the winter to exaggerate any potential drying effect. The lotion was rated positively in all cosmetic categories surveyed including overall feel, lack of oiliness, moisturization, smoothness during application, and feel while washing.

Example 16

Polyglyceryl Ester Containing Thickener Systems

The following compositions were prepared by heating the thickener system and the solvent in separate jars to 75° C., rapidly adding the solvent to the thickeners, shaking vigorously, and stirring with an overhead stirrer for 10 minutes while immersed in a 10–15° C. water bath. The Tm was measured as described above.

|  | Sample | | | | |
| --- | --- | --- | --- | --- | --- |
|  | A | B | C | D | E |
| Component | Amount (grams) | | | | |
| Decaglyn 1-S[1] | 1.5 | 1.5 | 1.5 | | |
| Polyaldo 10-1-S[2] | | | | 1.5 | 1.5 |
| Brij 76[3] | 0.5 | 0.5 | 0.5 | 0.5 | 0.5 |
| Lanette 22[4] | 0.25 | 0.25 | 0.5 | | |
| Lanette 18[5] | 0.25 | 0.25 | | | |
| Incroquat DBM90[6] | | | | 0.56 | 0.50 |
| Kemester 9022[7] | | | 0.5 | | |
| Promyristyl PM3[8] | | 0.5 | 0.75 | | |
| Arcol PPG-425[9] | | | | | 2.0 |
| Procetyl 50[10] | | | | | 2.0 |
| 200 Proof Ethanol/water 68:32 | 47.5 | 46.75 | 46.25 | 47.44 | 43.63 |
| Tm(° C.) | 36 | 32 | 40 | 43–48 | 40–44 |

[1]Decaglyn 1-S = decaglycerolmonostearate, Barnet of Paterson, NJ.
[2]Polyaldo 10-1-S = decaglycerolmonostearate, Lonza of Fairlawn, NJ.
[3]Brij 76 = steareth-10, ICI Surfactants of Wilmington, DE.
[4]Lanette 22 = behenyl alcohol, Henkel Corp. of Hoboken, NJ.
[5]Lanette 18 = stearyl alcohol, Henkel Corp. of Hoboken, NJ.
[6]Incroquat DBM90 = dibehenyldimethyl ammonium methosulfate, Croda Inc. Parsippany, NJ.
[7]Kemester 9022 = methyl behenate, Witco, Humko Chemical Div. of Memphis, TN.
[8]Promyristyl PM-3 = PPG-3 myristyl ether, Croda of Parsippany, NJ.
[9]Arcol PPG-425 = polypropylene glycol, MW = approximately 450, Arcol Chemical Co.
[10]Procetyl 50 = PPG-50 cetyl ether, Croda Inc.

Samples A and B were homogenous viscous and translucent creams. Sample C was similar but of higher viscosty and somewhat pearlescent. Samples D and E were homogenous viscous translucent almost gel-like compositions. The Tm values of Samples A and B indicate that the Promyristyl PM3 emollient decreased the melt temperature of the formulations. Sample E had a fairly nice feel but was a little tacky.

Comparative Examples 17–21

Samples were prepared according to compositions and the methods taught in U.S. Pat. No. 4,956,170 ("'170 patent") except that the polymeric thickening agents required in the '170 patent were omitted in order to compare the polymer-free viscosities of the '170 Example compositions with those of this invention. These Comparative Examples demonstrate that the compositions and procedures disclosed in the '170 patent do not produce desirable compositions if the polymeric viscosifiers are omitted from the compositions.

Comparative Example 17

Example 1 of U.S. Pat. No. 4,956,170 without the ACRITAMER 940 and JAGUAR HP-120

| Ingredient | Amount (grams) |
| --- | --- |
| Ethanol Anhydrous | 43.40 |
| Cetyl Alcohol | 1.17 |
| Myristyl Alcohol | 0.23 |
| Isopropyl Palmitate | 0.70 |
| Dow Corning 225 | 0.06 |

-continued

| Ingredient | Amount (grams) |
| --- | --- |
| Glycerine | 2.80 |
| Petrolatum | 0.93 |
| BRIJ 58 | 0.12 |
| Deionized Water | 19.75 |

To a 4 oz. glass jar, the ethanol and isopropyl palmitate were added. The jar was then swirled to dissolve the components. To a second 4 oz. glass jar, the water was added followed by the Dow Corning 225 fluid, glycerine, petrolatum, cetyl alcohol and myristyl alcohol. The jar and its contents were heated to 58° C. until all the ingredients were liquefied. The BRIJ 58 was then added to the second jar. The solution in the second jar was then heated to 58° C. and homogenized using a Silverson Homogenizer equipped with a 1 inch square hole head at high speed for 30 seconds. The jar was then capped and cooled under cold running water until the contents reached ambient temperature. The alcohol solution was then added to the aqueous phase and the resulting solution was homogenized at the lowest speed for 30 seconds.

The viscosity of the solution was high and nearly gelled before the ethanol was added. Once the ethanol was added the formulation was unstable and separated with white clumps floating and adhering to the walls of the container.

Comparative Example 18

Example 2 of U.S. Pat. No. 4,956,170 without the ACRITAMER 940 and JAGUAR HP-120

| Ingredient | Amount (grams) |
| --- | --- |
| Ethanol Anhydrous | 43.40 |
| Stearyl Alcohol | 0.88 |
| Isopropyl Palmitate | 0.53 |
| Dow Corning 225 | 0.04 |
| Glycerine | 2.10 |
| Petrolatum | 0.70 |
| BRIJ 58 | 0.80 |
| Deionized Water | 21.32 |

To a 4 oz. glass jar, the ethanol and isopropyl palmitate were added. The jar was then swirled to dissolve the components. To a second 4 oz. glass jar, the water was added followed by the Dow Corning 225 fluid, glycerine, petrolatum, and stearyl alcohol. The jar and its contents were heated to 66° C. until all the ingredients were liquefied. The BRIJ 58 was then added to the second jar. The solution in the second jar was then heated to 66° C. and homogenized using a Silverson Homogenizer equipped with a 1 inch square hole head at high speed for 30 seconds. The jar was then capped and cooled under cold running water until the contents reached ambient temperature. The alcohol solution was then added to the aqueous phase and the resulting solution was homogenized at the lowest speed for 30 seconds.

Before the alcohol was added the composition was a white solution with low viscosity. Once the alcohol was added the formulation became unstable and separated with white clumps floating, settling to the bottom and adhering to the walls of the container.

Comparative Example 19

Example 5 of U.S. Pat. No. 4,956,170 without the ACRITAMER 940, Fragrance and Dyes

| Ingredient | Amount (by weight) |
| --- | --- |
| Ethanol Anhydrous | 45.50 |
| Isopropyl Palmitate | 0.70 |
| Petrolatum | 0.70 |
| BRIJ 721 | 0.07 |
| Deionized Water | 22.11 |

To a 4 oz. glass jar, the water, petrolatum, isopropyl palmitate and the BRIJ 721 were added. The jar was then heated to 58° C. until all ingredients were liquefied. The solution was then homogenized using a Silverson Homogenizer equipped with a 1 inch square hole head at high speed for 30 seconds. The jar was then capped and cooled under cold running water until the contents reached ambient temperature. The alcohol solution was then added to the aqueous phase and the resulting solution was homogenized at the lowest speed for 30 seconds.

Before the alcohol was added the material was a low viscosity solution. Once the alcohol was added the formulation separated with white clumps adhering to the walls of the container.

Comparative Example 20

Example 7 of U.S. Pat. No. 4,956,170 without the ACRITAMER 940 and Fragrance

| Ingredient | Amount (grams) |
| --- | --- |
| Ethanol Anhydrous | 43.40 |
| Stearyl Alcohol | 1.75 |
| Isopropyl Palmitate | 0.42 |
| Dow Corning 225 | 0.04 |
| Glycerine | 1.68 |
| Petrolatum | 0.56 |
| BRIJ 58 | 0.18 |
| Deionized Water | 21.27 |

To a 4 oz. glass jar, the water, isopropyl palmitate, Dow Corning 225 Fluid, glycerine, petrolatum, BRIJ 58 and stearyl alcohol were added. The jar and its contents were heated to 77° C. until all the ingredients were liquefied. The solution in the jar was then homogenized using a Silverson Homogenizer equipped with a 1 inch square hole head at high speed for 30 seconds. The jar was then capped and cooled under cold running water until the contents reached ambient temperature. The alcohol was then added to the aqueous phase and the resulting solution was homogenized at the lowest speed for 30 seconds.

The viscosity of the solution was high and was nearly gelled before the ethanol was added. Once the alcohol was added the formulation became unstable and separated with white clumps floating, settling to the bottom and adhering to the walls of the container.

Comparative Example 21

Example 21 of U.S. Pat. No. 4,956,170 without the ACRITAMER 940

| Ingredient | Amount (grams) |
| --- | --- |
| Ethanol Anhydrous | 43.40 |
| Cetyl Alcohol | 1.05 |
| Myristyl Alcohol | 0.53 |
| Isopropyl Palmitate | 1.05 |
| Dow Corning 225 | 0.09 |
| Glycerine | 4.20 |
| Petrolatum | 1.40 |
| BRIJ 58 | 0.14 |
| Deionized Water | 17.43 |

To a 4 oz. glass jar, the water, isopropyl palmitate, Dow Corning 225 Fluid, glycerine, petrolatum, cetyl alcohol, myristyl alcohol and BRIJ 58 were added. The jar and its contents were heated to 66° C. until all the ingredients were liquefied. The solution in the jar was then homogenized using a Silverson Homogenizer equipped with a 1 inch square hole head at high speed for 30 seconds. The jar was then capped and cooled under cold running water until the contents reached ambient temperature. The alcohol was then added to the aqueous phase and the resulting solution was homogenized at the lowest speed for 30 seconds.

The viscosity of the solution was high and nearly gelled before the ethanol was added. Once the alcohol was added the formulation was unstable and separated with white clumps floating and adhering to the walls of the container.

Comparative Examples 22 and 23

Samples were prepared according to the compositions and methods taught in U.S. Pat. No. 5,167,950 ("950" patent) which is hereby incorporated by reference. The samples were prepared according to the '950 patent except that the polymeric thickening agents and propellants required in the '950 patent were omitted in order to compare the polymer free lotion viscosities of the '950 patent Example compositions with those of this invention. These Comparative Examples demonstrate that a relatively high concentration of short chain emulsifiers is required to achieve a desirable viscosity. Further, the viscosities of these Comparative Example Samples do not appear to be stable over time.

Comparative Example 22

Example 7 of U.S. Pat. No. 5,167,950 without the Carbomer 951, triethanolamine, fragrance

| Ingredient | Amount (grams) |
| --- | --- |
| 200 proof Ethanol | 144.0 |
| Deionized water | 82.80 |
| Ritapro 300 | 6 |
| Brij 721 | 1.5 |
| Brij 72 | 4.5 |

To an 8oz. glass jar, the ethanol and water were added and mixed together and heated to 60° C. The Ritapro 300, Brij 72 and Brij 721 were added and the contents kept at 60° C. until the waxes melted. The mixture was stirred and allowed to cool to ambient temperature. The viscosity was determined as a function of time. The viscosity was measured using a Brookfield LVDV-I+ with a heliopath adapter and spindle T–C. The spindle speed is as indicated below:

| Time (days) | Viscosity (cps) | Spindle Speed (rpm) |
|---|---|---|
| initial | 29,190 | 1.5 |
| 1 | 26,000 | 1.5 |
| 2 | 24,130 | 1.5 |
| 6 | 23,560 | 1.5 |
| 7 | 24,000 | 1.5 |
| 8 | 22,250 | 1.5 |
| 19 | 20,880 | 1.5 |

This formulation has an initial viscosity of only 29,190 cps even though the sample includes 5% by weight emulsifier in the thickener system.

Comparative Example 23

Example 15 of U.S. Pat. No. 5,167,950 without the Carbomer 951, triethanolamine, fragrance

| Ingredient | Amount (grams) |
|---|---|
| 200 proof Ethanol | 144.0 |
| Deionized water | 82.80 |
| Ritapro 300 | 9.0 |
| Lactodan P22 | 3.0 |

To an 8oz. glass jar, the ethanol and water were added and mixed together and heated to 60° C. The Ritapro 300 and Lactodan P22 were added and the contents kept at 60° C. until the waxes melted. The mixture was stirred and allowed to cool to ambient temperature. The viscosity was determined as a function of time. The viscosity was measured using a Brookfield LVDV-I+ with a heliopath adapter and spindle T–C. The spindle speed was as indicated below:

| Time (days) | Viscosity (cps) | Spindle Speed (rpm) |
|---|---|---|
| initial | 144,700 | 0.3 |
| 1 | 146,900 | 0.3 |
| 2 | 123,800 | 0.3 |
| 6 | 134,500 | 0.3 |
| 7 | 107,800 | 0.3 |
| 8 | 71,250 | 0.3 |
| 19 | 42,810 | 0.6 |

The viscosity of this formulation dropped rapidly and after 19 days had decreased to only 29.6% of the initial value.

Example 24

Alkyl Alcohol/Long Chain Polyethoxylate Thickener System

The following formulation was prepared using the compounds listed below in the percentages indicated.

| Ingredient Number | Ingredient | wt. Percent |
|---|---|---|
| Part A | | |
| 1 | Beheneth Ether[1] (BB-10) | 1.50 |
| 2 | Unithox 470[2] | 0.25 |
| 3 | Behenyl Alcohol[3] (BE-22) | 1.10 |
| 4 | Cetyl Palmitate[4] | 0.05 |
| 5 | Diisopropyl Dimerate[5] | 1.00 |
| 6 | Squalane[6] | 1.00 |
| 7 | Dimethicone L45/350[7] | 0.50 |
| Part B | | |
| 8 | Polyethylene Glycol 900[8] | 0.95 |
| 9 | Polyethylene Glycol 600[9] | 0.30 |
| 10 | Glycerol[10] | 0.45 |
| 11 | Purified Water | 21.85 |
| Part C | | |
| 12 | Ethyl Alcohol[11] | 65.78 |
| 13 | Chlorhexidine Gluconate[12] solution | 5.27 |

[1]Beheneth-10 as Nikkol BB-10 available from Barnet Products Corporation, Englewood Cliffs, NJ
[2]Unithox 470 available from Petrolite Specialty Polymers Group, Tulsa, OK
[3]Behenyl alcohol as Cachelot BE-22 available from M. Michel & Company, Inc, New York, NY
[4]Cetyl palmitate as Crodamol CP available from Croda, Inc. Parsippany, NY
[5]Diisopropyldilineolate as Pripure 3786 from Unichema North America, Chicago, Ill.
[6]Squalane as Phytolane from Barnet Products Corporation, Englewood Cliffs, NJ
[7]Dimethicone L45/350 from OSI Specialties, Inc. Danbury, CT
[8]Polyethylene glycol 900 from Dow Chemical, Midland, MI
[9]Polyethylene glycol 600 as Carbowax 600 from Union Carbide
[10]Glycerol as Optim from Dow Chemical, Midland, MI
[11]Ethanol was 190 proof from Aaper Shelbyville, KY
[12]Chlorhexidine, Medichem, Barcelona, Spain 20.1% wt/vol. in water The composition was prepared in an overall batch size of 1200 g by placing the ingredients of Part A into a one gallon glass jar and the ingredients of Part B into a one quart glass jar. These were nitrogen purged for 20 seconds and sealed prior to heating to 90° C. in an oven. Both parts were heated until Part A was melted (about 2 hours). Part B was added to Part A and homogenized using the Silverson homogenizer with large head and fine screen at a medium speed. This was allowed to cool. Part C was placed in a one quart jar and slowly added to the cooled combined formulation using the homogenizer on low speed. Once all of part C was added the contents were further homogenized at medium speed until to composition appeared homogenous.

This formula was applied by numerous volunteers and found to have very nice cosmetic properties.

While in accordance with the patent statutes, description of the preferred weight fractions, processing conditions, and product usages have been provided, the scope of the invention is not intended to be limited thereto or thereby. Various modifications and alterations of the present invention will be apparent to those skilled in the art without departing from the scope and spirit of the present invention. The Examples described in this application are illustrative of the possibilities of varying the type, quantity and ratio of composition as well as the methods for making formulations of the present invention. The complete disclosures of all patents, patent applications, and publications recited herein are incorporated by reference, as if individually incorporated by reference.

What is claimed is:

1. A hydroalcoholic composition comprising:
   a) a major amount of a hydroalcoholic solvent comprising a lower alcohol and water in a weight ratio of about 60:40 to about 75:25; and
   b) a thickener system present in an amount of about 0.5% by weight to about 8% by weight, based on the total weight of the composition; wherein the thickener system comprises at least one emulsifier in an amount of at least about 0.05% by weight, based on the total weight of the composition; wherein the emulsifier comprises:
      (i) at least one hydrophobic group selected from the group of:
         (A) an alkyl group of at least 16 carbon atoms;
         (B) an alkenyl group of at least 16 carbon atoms; and
         (C) an aralkyl or an aralkenyl group of at least 20 carbon atoms; and
      (ii) at least one hydrophilic group selected from the group of:
         (A) an ethylene oxide- and/or propylene oxide-containing group bonded to the hydrophobic group through an ether or ester bond and optionally terminated with a (C1–C36)alkyl ester, (C2–C36)alkenyl ester, or (C6–C36)alkaryl ester;
         (B) an alcohol group;
         (C) a polyhydric alcohol group;
         (D) an ester or ether group of a polyhydric alcohol or polyalkoxylated derivative thereof;
         (E) an ester or ether group of sorbitan or polyalkoxylated derivative thereof having 2–150 moles of alkylene oxide per mole of hydrophobic group; and
         (F) combinations thereof,
   wherein;
   the composition has a melt temperature of greater than about 35° C. when in the absence of an auxiliary thickener and a viscosity of at least about 4,000 centipoise at 23° C. when in the absence of an auxiliary thickener;
   wherein the viscosity is measured using a very low shear viscometer and T spindles with a heliopath adapter.

2. The composition of claim 1 further comprising at least one emollient distinct from the thickener system.

3. The composition of claim 2 wherein the at least one emollient is in the form of a wax or a liquid.

4. The composition of claim 1 further comprising an antimicrobial agent distinct from the lower alcohol.

5. The composition of claim 4 wherein the antimicrobial agent is selected from the group of a chlorhexidine salt, iodine, a complexed form of iodine, parachlorometaxylenol, triclosan, hexachlorophene, Lauricidin, a phenol, a surfactant having a long chain hydrophobic group and a quaternary group, a quaternary silane, hydrogen peroxide, silver, a silver salt, silver oxide, silver sulfadiazine, and mixtures thereof.

6. The composition of claim 1 wherein the emulsifier is selected from the group of a poly(ethoxylated and/or propoxylated)alcohol, a poly(ethoxylated and/or propoxylated)ester, a derivative of a poly(ethoxylated and/or propoxylated)alcohol, a derivative of a poly(ethoxylated and/or propoxylated)ester, an alkyl alcohol, an alkenyl alcohol, an ester of a polyhydric alcohol, an ether of a polyhydric alcohol, an ester of a polyalkoxylated derivative of a polyhydric alcohol, an ether of a polyalkoxylated derivative of a polyhydric alcohol, a sorbitan fatty acid ester, a polyalkoxylated derivative of a sorbitan fatty acid ester, and mixtures thereof.

7. The composition of claim 1 wherein the thickener system comprises one or more emulsifiers capable of forming an alcoholic composition having a viscosity of at least about 4,000 centipoise at 23° C. when in the absence of an auxiliary thickener, wherein the very low shear viscometer is a Brookfield LVDV-I$^+$ equipped with a model D Brookfield heliopath and T spindles B–F.

8. The composition of claim 1 further comprising a polymeric thickening agent.

9. The composition of claim 1 wherein the emulsifier includes at least two hydrophobic groups.

10. The composition of claim 1 wherein at least one of the emulsifiers is a solid at room temperature and the thickener system hydrophobe number average chain length is at least about 20.

11. The composition of claim 1 which has a melt temperature of greater than about 40° C. when in the absence of an auxiliary thickener.

12. A lotion comprising:
   a) a major amount of a solvent comprising a lower alcohol and water in a weight ratio of about 60:40 to 100:0;
   b) a thickener system present in an amount of about 0.5% by weight to about 8% by weight, based on the total weight of the lotion; wherein the thickener system comprises at least two emulsifiers, each in an amount of at least about 0.05% by weight, based on the total weight of the lotion; wherein at least one of the emulsifiers comprises:
      (i) at least one hydrophobic group selected from the group of:
         (A) an alkyl group of at least 16 carbon atoms;
         (B) an alkenyl group of at least 16 carbon atoms; and
         (C) an aralkyl or an aralkenyl group of at least 20 carbon atoms; and
      (ii) at least one hydrophilic group selected from the group of:
         (A) an ethylene oxide- and/or propylene oxide-containing group bonded to the hydrophobic group through an ether or ester bond and optionally terminated with a (C1–C36)alkyl ester, (C2–C36)alkenyl ester, or (C6–C36)alkaryl ester;
         (B) an ester or ether group of a polyalkoxylated polyhydric alcohol;
         (C) an ester or ether group of a polyalkoxylated sorbitan having 2–150 moles of alkylene oxide per mole of hydrophobic group; and
         (D) combinations thereof;
            wherein at least one of the other emulsifiers comprises:
      (i) at least one hydrophobic group selected from the group of:
         (A) an alkyl group of at least 16 carbon atoms;
         (B) an alkenyl group of at least 16 carbon atoms; and
         (C) an aralkyl or an aralkenyl group of at least 20 carbon atoms; and
      (ii) at least one alcoholic or polyhydroalcoholic hydrophilic group; and c) an antimicrobial agent distinct from the lower alcohol;
wherein:

the lotion has a melt temperature of greater than about 35° C. when in the absence of an auxiliary thickener and the at least two emulsifiers provide the lotion with a viscosity of at least about 4,000 centipoise at 23° C. when in the absence of an auxiliary thickener;

wherein the viscosity is measured using a very low shear viscometer and T spindles with a heliopath adapter.

13. The lotion of claim 12 wherein the thickener system comprises one or more emulsifiers capable of forming an alcoholic lotion having a viscosity of at least about 4,000 centipoise at 23° C. when in the absence of an auxiliary thickener, wherein the very low shear viscometer is a Brookfield LVDV-I+ equipped with a model D Brookfield heliopath and T spindles B–F.

14. A lotion comprising:
  a) a major amount of a solvent comprising a lower alcohol and water in a weight ratio of about 60:40 to about 100:0; and
  b) a thickener system present in an amount of about 0.5% by weight to about 8% by weight, based on the total weight of the lotion; wherein the thickener system comprises at least one emulsifier in an amount of at least about 0.05% by weight, based on the total weight of the lotion; wherein the emulsifier comprises:
    (i) at least one hydrophobic group selected from the group of:
      (A) an alkyl group of at least 20 carbon atoms;
      (B) an alkenyl group of at least 20 carbon atoms; and
      (C) an aralkyl or an aralkenyl group of at least 20 carbon atoms; and
    (ii) at least one hydrophilic group selected from the group of:
      (A) an ethylene oxide- and/or propylene oxide-containing group which is bonded to the hydrophobic group through an ether or ester bond and optionally terminated with a (C1–C36)alkyl ester, (C2–C36)alkenyl ester, or (C6–C36)alkaryl ester;
      (B) an alcohol group;
      (C) a polyhydric alcohol group;
      (D) an ester or ether group of a polyhydric alcohol or polyalkoxylated derivative thereof;
      (E) an ester or ether group of sorbitan or polyalkoxylated derivative thereof having 2–150 moles of alkylene oxide per mole of hydrophobic group; and
      (F) combinations thereof; and
  c) a chlorhexidine salt;
wherein:

the at least one emulsifier provides the lotion with a melt temperature of greater than about 25° C. when in the absence of an auxiliary thickener and a viscosity of at least about 4,000 centipoise at 23° C. when in the absence of an auxiliary thickener;

wherein the viscosity is measured using a very low shear viscometer and T spindles with a heliopath adapter.

15. The lotion of claim 14 wherein the thickener system comprises one or more emulsifiers capable of forming an alcoholic lotion having a viscosity of at least about 4,000 centipoise at 23° C. when in the absence of an auxiliary thickener, wherein the very low shear viscometer is a Brookfield LVDV-I+ equipped with a model D Brookfield heliopath and T spindles B–F.

16. A method of preparing a stable hydroalcoholic composition, the method comprising:
  a) heating a thickener system to a temperature sufficient to melt it; the thickener system comprising at least one emulsifier in an amount of at least about 0.05% by weight, based on the total weight of the composition; wherein the emulsifier comprises:
    (i) at least one hydrophobic group selected from the group of:
      (A) an alkyl group of at least 16 carbon atoms;
      (B) an alkenyl group of at least 16 carbon atoms; and
      (C) an aralkyl or an aralkenyl group of at least 20 carbon atoms; and
    (ii) at least one hydrophilic group selected from the group of:
      (A) an ethylene oxide- and/or propylene oxide-containing group bonded to the hydrophobic group through an ether or ester bond and optionally terminated with a (C1–C36)alkyl ester, (C2–C36)alkenyl ester, or (C6–C36)alkaryl ester;
      (B) an alcohol group;
      (C) a polyhydric alcohol group;
      (D) an ester or ether group of a polyhydric alcohol or polyalkoxylated derivative thereof;
      (E) an ester or ether group of sorbitan or polyalkoxylated derivative thereof having 2–150 moles of alkylene oxide per mole of hydrophobic group; and
      (F) combinations thereof;
  b) heating water to a temperature above the melt temperature of the thickener system;
  c) combining the thickener system and the water; and
  d) adding a lower alcohol to the thickener system and water to form a composition comprising a major amount of a hydroalcoholic solvent system comprising a lower alcohol and water; wherein the composition has a melt temperature of greater than about 35° C. when in the absence of an auxiliary thickener and a viscosity of at least about 4,000 centipoise at 23° C. when in the absence of an auxiliary thickener; wherein the viscosity is measured using a very low shear viscometer and T spindles with a heliopath adapter; wherein the lower alcohol and water are present in a weight ratio of about 60:40 to about 75:25.

17. A method of preparing a lotion comprising:
  a) heating a thickener system comprising at least two emulsifiers each in an amount of at least about 0.05% by weight, based on the total weight of the lotion; wherein at least one of the emulsifiers comprises:
    (i) at least one hydrophobic group selected from the group of:
      (A) an alkyl group of at least 16 carbon atoms;
      (B) an alkenyl group of at least 16 carbon atoms; and
      (C) an aralkyl or an aralkenyl group of at least 20 carbon atoms; and
    (ii) at least one hydrophilic group selected from the group of:
      (A) an ethylene oxide- and/or propylene oxide-containing group bonded to the hydrophobic group through an ether or ester bond and optionally terminated with a (C1–C36)alkyl ester, (C2–C36)alkenyl ester, or (C6–C36)alkaryl ester;
      (B) an ester or ether group of a polyalkoxylated polyhydric alcohol;
      (C) an ester or ether group of polyalkoxylated sorbitan having 2–150 moles of alkylene oxide per mole of hydrophobic group; and
      (D) combinations thereof; and wherein at least one of the other emulsifiers comprises:
  (i) at least one hydrophobic group selected from the group of:
    (A) an alkyl group of at least 16 carbon atoms;
    (B) an alkenyl group of at least 16 carbon atoms; and
    (C) an aralkyl or an aralkenyl group of at least 20 carbon atoms; and
  (ii) at least one alcoholic or polyhydroalcoholic hydrophilic group;
b) combining the thickener system and a major amount of an alcoholic solvent system comprising a lower alcohol and an antimicrobial agent distinct from the lower alcohol to form a lotion having a melt temperature of greater than about 35° C. when in the absence of an auxiliary thickener and a viscosity of at least about 4,000 centipoise at 23° C. when in the absence of an auxiliary thickener; wherein the viscosity is measured using a very low shear viscometer and T spindles with a heliopath adapter; wherein the alcoholic solvent system comprises a lower alcohol and water in a weight ratio of about 60:40 to about 100:0.

18. A hydroalcoholic lotion comprising:
a) a major amount of a hydroalcoholic solvent comprising a lower alcohol and water in a weight ratio of about 60:40 to about 75:25; and
b) a thickener system present in an amount of about 0.5% by weight to about 8% by weight, based on the total weight of the lotion; wherein the thickener system comprises at least one emulsifier in an amount of at least about 0.05% by weight, based on the total weight of the lotion; wherein the emulsifier comprises:
  (i) at least one hydrophobic group selected from the group of:
    (A) an alkyl group of at least 16 carbon atoms;
    (B) an alkenyl group of at least 16 carbon atoms; and
    (C) an aralkyl or an aralkenyl group of at least 20 carbon atoms; and
  (ii) at least one hydrophilic group selected from the group of:
    (A) an ethylene oxide- and/or propylene oxide-containing group bonded to the hydrophobic group through an ether or ester bond and optionally terminated with a (C1–C36)alkyl ester, (C2–C36)alkenyl ester, or (C6–C36)alkaryl ester;
    (B) an alcohol group;
    (C) a polyhydric alcohol group;
    (D) an ester or ether group of a polyhydric alcohol or polyalkoxylated derivative thereof;
    (E) an ester or ether group of sorbitan or polyalkoxylated derivative thereof having 2–150 moles of alkylene oxide per mole of hydrophobic group; and
    (F) combinations thereof
wherein:
  the lotion has a melt temperature of greater than about 35° C. when in the absence of an auxiliary thickener; and
  the at least one emulsifier provides the lotion with a viscosity of at least about 4,000 centipoise at 23° C. when in the absence of an auxiliary thickener; wherein the viscosity is measured using a very low shear viscometer and T spindles with a heliopath adapter.

19. A hydroalcoholic composition comprising:
a) a major amount of a hydroalcoholic solvent comprising a lower alcohol and water in a weight ratio of about 40:60 to about 95:5; and
b) a thickener system present in an amount of about 0.5% by weight to about 8% by weight, based on the total weight of the composition; wherein the thickener system comprises at least one emulsifier in an amount of at least about 0.05% by weight, based on the total weight of the composition; wherein the emulsifier comprises:
  (i) at least one hydrophobic group selected from the group of:
    (A) an alkyl group of at least 16 carbon atoms;
    (B) an alkenyl group of at least 16 carbon atoms; and
    (C) an aralkyl or an aralkenyl group of at least 20 carbon atoms; and
  (ii) at least one hydrophilic group selected from the group of:
    (A) an ethylene oxide- and/or propylene oxide-containing group bonded to the hydrophobic group through an ether or ester bond and optionally terminated with a (C1–C36)alkyl ester, (C2–C36)alkenyl ester, or (C6–C36)alkaryl ester;
    (B) an alcohol group;
    (C) a polyhydric alcohol group;
    (D) an ester or ether group of a polyhydric alcohol or polyalkoxylated derivative thereof;
    (E) an ester or ether group of sorbitan or polyalkoxylated derivative thereof having 2–150 moles of alkylene oxide per mole of hydrophobic group; and
    (F) combinations thereof;
wherein:
  the composition has a melt temperature of greater than about 35° C. when in the absence of an auxiliary thickener and a viscosity of at least about 20,000 centipoise at 23° C. when in the absence of an auxiliary thickener;
wherein the viscosity is measured using a very low shear viscometer and T spindles with a heliopath adapter.

* * * * *

UNITED STATES PATENT AND TRADEMARK OFFICE
CERTIFICATE OF CORRECTION

PATENT NO.    : 6,534,069 B1
DATED         : March 18, 2003
INVENTOR(S)   : Asmus, Robert A.

It is certified that error appears in the above-identified patent and that said Letters Patent is hereby corrected as shown below:

Title Page,
Item (56), References Cited, OTHER PUBLICATIONS "Bulletin No. 51-0001-259" reference, delete "Wilimington" and insert in place thereof -- Wilmington --.

Column 1,
Lines 9-11, delete "This application is a continuation-in-part of application Ser. No. 8/493,695, filed Jun. 22, 1995, abandoned incorporated herein by reference.".

Column 2,
Line 16, after "polymeric" insert -- gelling --.
Line 17, delete "uprising" and insert in place thereof -- comprising --.

Column 5,
Line 43, delete "entitled." and insert in place thereof -- entitled, --.

Column 7,
Line 4, delete "hydrophobe" (first occurrence) and insert in place thereof
-- hydrophobe, --.
Line 6, delete "alkenyl ester" and insert in place thereof -- alkenyl ester, --.
Lines 6-7, delete "alkaryl ester; (i.e., aralkyl ester)" and insert in place thereof -- alkaryl ester (i.e., aralkyl ester); --.
Line 7, delete "alcohol," and insert in place thereof -- alcohol; --.

Column 8,
Line 35, delete "surfactant, (i.e., emulsifier)" and insert in place thereof -- surfactant (i.e., emulsifier), --.

Column 9,
Line 22, delete "R''',"  and insert in place thereof -- R''' ; --.
Line 34, delete "polyethyoxylated" and insert in place thereof -- polyethoxylated --.
Line 40, delete "Thereof" and insert in place thereof -- thereof --.
Line 44, delete "$R_6(C(O))_pO(CH_2CH_2O)_m(CH_2CHO)_rR_($" and insert in place thereof
-- $R_6(C(O))_pO(CH_2CH_2O)_m(CH_2CHO)_rR_8$ --.

Column 10,
Lines 19-20, delete "M Michel" and insert in place thereof -- M. Michel --.

UNITED STATES PATENT AND TRADEMARK OFFICE
CERTIFICATE OF CORRECTION

PATENT NO.     : 6,534,069 B1
DATED          : March 18, 2003
INVENTOR(S)    : Asmus, Robert A.

It is certified that error appears in the above-identified patent and that said Letters Patent is hereby corrected as shown below:

Column 14,
Line 8, delete "polyary/alkylsiloxanes," and insert in place thereof
-- polyaryl/alkylsiloxanes, --.

Column 17,
Line 6, delete "Lauricidin;" and insert in place thereof -- Lauricidin, --.

Column 18,
Line 32, delete "shearixing" and insert in place thereof -- shear mixing --.

Column 20,
Line 21, delete "demonstrate hat" and insert in place thereof -- demonstrates that --.

Column 21,
Line 58, delete "polyethyoxylated" and insert in place thereof -- polyethoxylated --.

Column 24,
Line 19, delete "below" and insert in place thereof -- below. --.

Column 25,
Line 1, beneath the Table, delete "(C2" and insert in place thereof -- (C22 --.

Column 31,
Line 39, in the Table "Viscosity at Given Temperature" under column "40°C" and column "cps" under Sample I, delete "10.250" and insert in place thereof -- 10,250 --.

Column 32,
Line 35, delete "coemulsifing" and insert in place thereof -- coemulsifying --.

Column 34,
Line 18, delete "palirtate," and insert in place thereof -- palmitate, --.

Column 35,
Line 35, delete "viscosty" and insert in place thereof -- viscosity --.

UNITED STATES PATENT AND TRADEMARK OFFICE
CERTIFICATE OF CORRECTION

PATENT NO. : 6,534,069 B1
DATED : March 18, 2003
INVENTOR(S) : Asmus, Robert A.

It is certified that error appears in the above-identified patent and that said Letters Patent is hereby corrected as shown below:

Column 41,
Line 41, delete "thereof," and insert in place thereof -- thereof; --.
Line 42, delete "wherein;" and insert in place thereof -- wherein: --.

Column 45,
Line 54, delete "thereof" and insert in place thereof -- thereof; --.

Signed and Sealed this

Thirteenth Day of September, 2005

JON W. DUDAS
*Director of the United States Patent and Trademark Office*

UNITED STATES PATENT AND TRADEMARK OFFICE
CERTIFICATE OF CORRECTION

PATENT NO. : 6,534,069 B1  Page 1 of 1
APPLICATION NO. : 09/327978
DATED : March 18, 2003
INVENTOR(S) : Asmus et al.

It is certified that error appears in the above-identified patent and that said Letters Patent is hereby corrected as shown below:

In column 10, lines 43-49, after "Class 4, Sorbitan Fatty Acid Esters," please delete the existing structure and insert the following structure therefore:

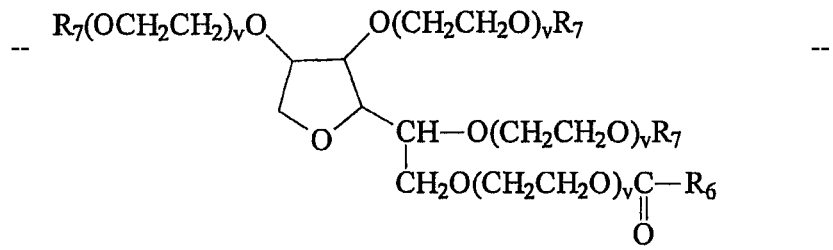

Signed and Sealed this

Thirteenth Day of July, 2010

David J. Kappos
*Director of the United States Patent and Trademark Office*